United States Patent
Fries et al.

(10) Patent No.: US 9,428,438 B2
(45) Date of Patent: Aug. 30, 2016

(54) PROCESS FOR PREPARING FORMIC ACID

(71) Applicant: BASF SE, Ludwigshafen (DE)

(72) Inventors: Donata Maria Fries, Mannheim (DE); Klaus-Dieter Mohl, Hockenheim (DE); Martin Schäfer, Grünstadt (DE); Daniel Schneider, Frankenthal (DE); Peter Bassler, Viernheim (DE); Stefan Rittinger, Mannheim (DE); Joaquim Henrique Teles, Waldsee (DE)

(73) Assignee: BASF SE, Ludwigshafen (DE)

( * ) Notice: Subject to any disclaimer, the term of this patent is extended or adjusted under 35 U.S.C. 154(b) by 42 days.

(21) Appl. No.: 14/088,805

(22) Filed: Nov. 25, 2013

(65) Prior Publication Data

US 2014/0148617 A1 May 29, 2014

Related U.S. Application Data

(60) Provisional application No. 61/730,097, filed on Nov. 27, 2012.

(51) Int. Cl.
*C07C 53/02* (2006.01)
*C07C 51/44* (2006.01)
*C07C 51/02* (2006.01)

(52) U.S. Cl.
CPC .............. *C07C 51/44* (2013.01); *C07C 51/02* (2013.01)

(58) Field of Classification Search
CPC ...................................... C07C 53/02
USPC ......................................... 562/609
See application file for complete search history.

(56) References Cited

U.S. PATENT DOCUMENTS

| | | | |
|---|---|---|---|
| 4,217,460 A | 8/1980 | Hohenschutz et al. | |
| 4,218,568 A | 8/1980 | Hohenschutz et al. | |
| 5,294,740 A | 3/1994 | Kiefer et al. | |
| 8,835,683 B2 * | 9/2014 | Schneider et al. | 562/609 |
| 8,889,905 B2 * | 11/2014 | Bassler et al. | 562/609 |
| 8,901,350 B2 * | 12/2014 | Schneider et al. | 562/609 |
| 2008/0097126 A1 * | 4/2008 | Karl et al. | 562/609 |
| 2010/0126843 A1 | 5/2010 | Stabel et al. | |
| 2012/0157711 A1 | 6/2012 | Schaub et al. | |
| 2013/0012739 A1 | 1/2013 | Schaub et al. | |
| 2013/0090496 A1 | 4/2013 | Schaub et al. | |
| 2013/0123526 A1 | 5/2013 | Schaub et al. | |
| 2013/0190532 A1 | 7/2013 | Schneider et al. | |
| 2014/0018456 A1 | 1/2014 | Bassler et al. | |

FOREIGN PATENT DOCUMENTS

| | | | |
|---|---|---|---|
| CA | 2801580 | * | 1/2012 |
| CA | 2801580 A1 | | 1/2012 |
| DE | 2545658 A1 | | 4/1977 |
| DE | 3428319 A1 | | 2/1986 |
| DE | 102009046310 A1 | | 5/2010 |
| EP | 0 001 432 A1 | | 4/1979 |
| EP | 0563831 A2 | | 10/1993 |
| WO | WO-2006/021411 A1 | | 3/2006 |
| WO | WO-2012/000964 A1 | | 1/2012 |
| WO | WO-2012/084691 | | 6/2012 |
| WO | WO-2013/004577 | | 1/2013 |
| WO | WO-2013/050367 | | 4/2013 |
| WO | WO-2013/068389 | | 5/2013 |
| WO | WO-2013/092157 | | 6/2013 |
| WO | WO-2013/092403 | | 6/2013 |

* cited by examiner

*Primary Examiner* — Yong Chu
*Assistant Examiner* — Sonya Wright
(74) *Attorney, Agent, or Firm* — Drinker Biddle & Reath LLP

(57) ABSTRACT

Process for obtaining formic acid by thermal separation of a stream comprising formic acid and a tertiary amine (I), in which, in step (a), a liquid stream comprising formic acid, methanol, water and tertiary amine (I) is produced by combining methyl formate, water and tertiary amine (I), from there in step (b), methanol is separated off and in step (c), formic acid is removed by distillation from the liquid stream obtained in a distillation apparatus, wherein, when methyl formate, water and tertiary amine (I) are combined, methyl formate, water and optionally tertiary amine (I) are first introduced in step (a1) in a molar ratio of $0 \leq n(\text{amine to a1})/n(\text{mefo to a1}) \leq 0.1$, and from 70 to 100% of the hydrolysis equilibrium possible is set and then, in step (a2), tertiary amine (I) is introduced in a molar ratio of $0.1 \leq n(\text{amine to a2})/n(\text{mefo to a1}) \leq 2$, and the mixture is reacted.

19 Claims, 5 Drawing Sheets

PROCESS FOR PREPARING FORMIC ACID

CROSS-REFERENCE TO RELATED APPLICATIONS

This application claims benefit (under 35 USC 119(e)) of U.S. Provisional Application Ser. No. 61/730,097, filed Nov. 27, 2012, which is incorporated herein by reference in its entirety.

BACKGROUND OF THE INVENTION

The present invention relates to a process for obtaining formic acid by thermal separation of a stream comprising formic acid and a tertiary amine (I), which, at a pressure of 1013 hPa abs, has a boiling point which is at least 5° C. higher than that of formic acid, in which
a liquid stream comprising formic acid, methanol, water and tertiary amine (I) is produced by combining methyl formate, water and tertiary amine (I), from 10 to 100% by weight of the methanol comprised therein are separated off from the liquid stream obtained from step (a) and
formic acid is removed by distillation from the liquid stream comprising formic acid, water and tertiary amine (I) obtained from step (b) in a distillation apparatus at a temperature at the bottom of from 100 to 300° C. and a pressure of from 30 to 3000 hPa abs.

Formic acid is an important and versatile product. It is used, for example, for acidification in the production of animal feeds, as preservative, as disinfectant, as assistant in the textile and leather industry, as a mixture with its salts for deicing aircraft and runways and also as synthetic building block in the chemical industry.

The most widespread process at present for preparing formic acid is the hydrolysis of methyl formate which can be obtained, for example, from methanol and carbon monoxide. The aqueous formic acid obtained by hydrolysis is subsequently concentrated, for example using an extraction auxiliary such as a dialkylformamide (DE 25 45 658 A1).

In addition, obtaining formic acid by thermal dissociation of compounds of formic acid and a tertiary nitrogen base is also known. These compounds are generally acidic ammonium formates of tertiary nitrogen bases, in which the formic acid has reacted beyond the stage of classical salt formation with the tertiary nitrogen bases to form stable addition compounds bridged by hydrogen bonds. The addition compounds of formic acid and tertiary nitrogen bases can be formed by combining the tertiary nitrogen base and a formic acid source. Thus, for example, WO 2006/021,411 discloses the preparation of such addition compounds in general by (i) direct reaction of the tertiary nitrogen base with formic acid, (ii) by transition metal-catalyzed hydrogenation of carbon dioxide to formic acid in the presence of the tertiary nitrogen base, (iii) by reaction of methyl formate with water and subsequent extraction of the resulting formic acid by means of the tertiary nitrogen base and (iv) by reaction of methyl formate with water in the presence of the tertiary nitrogen base.

The general advantages of using addition compounds of formic acid and tertiary nitrogen bases for obtaining formic acid are that the addition compounds firstly bind the formic acid strongly enough to withdraw the formic acid from the medium, for example the reaction medium, in which the formic acid has been formed by chemical synthesis or, for example, from a dilute formic acid solution, and thereby allow the formic acid to be separated off more readily in the form of its addition compounds, but are weak enough for the formic acid subsequently to be able to be released again from the addition compounds by thermal dissociation in order to obtain it in concentrated and purified free form.

EP 0 001 432 A discloses a process for obtaining formic acid by hydrolysis of methyl formate in the presence of a tertiary amine, in particular an alkylimidazole, to form addition compounds of formic acid and the tertiary amine. The hydrolysis mixture obtained, which comprises unreacted methyl formate, water, methanol, addition compounds and tertiary amine, is freed of the low boilers methyl formate and methanol in a first distillation column. In a second column, the remaining bottom product is dewatered. The dewatered bottom product from the second column, which still comprises addition compounds and tertiary amine, is then fed to a third column and in this the addition compounds are thermally dissociated into formic acid and tertiary amine. The formic acid liberated is removed as overhead product. The tertiary amine collects in the liquid phase and is recirculated to the hydrolysis.

DE 34 28 319 A discloses a process for obtaining formic acid by hydrolysis of methyl formate. The hydrolysis mixture obtained, which comprises unreacted methyl formate, water, methanol and formic acid, is freed of the low boilers methyl formate and methanol in a first distillation column. The aqueous formic acid obtained at the bottom is subsequently extracted with a relatively high-boiling amine, in particular a relatively long-chain, hydrophobic $C_6$-$C_{14}$-trialkylamine, in the presence of an additional hydrophobic solvent, in particular an aliphatic, cycloaliphatic or aromatic hydrocarbon, and thereby converted into an aqueous addition compound of formic acid and the amine. This is dewatered in a second distillation column. The dewatered addition compound obtained at the bottom is then fed to a third distillation column and thermally dissociated therein. The hydrophobic solvent is present both in the overhead stream and the bottoms from the column. The gaseous overhead stream comprises mainly the formic acid liberated together with the hydrophobic solvent. This stream is liquefied again in the condenser. This results in formation of two phases, namely a polar formic acid phase and a hydrophobic solvent phase. The formic acid phase is discharged as product and the solvent phase is returned as runback to the column. Due to the presence of the hydrophobic solvent, complete dissociation of the adduct, which according to the teaching of the DE first publication occurs without decomposition of formic acid, can be achieved. The (virtually) formic acid-free bottoms comprise the hydrophobic amine and the hydrophobic solvent. This is recirculated to the extraction stage.

WO 2006/021,411 describes a process for obtaining formic acid by thermal dissociation of an addition compound of formic acid and a tertiary amine (quaternary ammonium formate), in which the tertiary amine has a boiling point of from 105 to 175° C. Alkylpyridines are mentioned as preferred tertiary amines. The specific boiling range of the tertiary amines increases the color stability of the formic acid obtained. The addition compound to be used can in general be obtained from the tertiary amine and a formic acid source. The output from the adduct synthesis is advantageously firstly freed of volatile constituents and then fed to the thermal dissociation. The thermal dissociation is carried out as usual in a distillation column. The formic acid liberated is removed as overhead product. The tertiary amine which may still comprise residues of formic acid collects in the liquid phase and can be recirculated to the formic acid source.

EP 0 563 831 A reports an improved process for the thermal dissociation of an addition compound of formic acid and a tertiary amine (quaternary ammonium formate) to give formic acid. The addition compound to be used can in general be obtained from the tertiary amine and a formic acid source. The output from the synthesis is advantageously firstly freed of volatile constituents and then fed to a distillation column for thermal dissociation. The improvement comprises essentially carrying out the thermal dissociation of the addition compound in the presence of a secondary formamide which increases the color stability of the formic acid obtained. The formic acid liberated is removed as overhead product. The tertiary amine and the secondary formamide collect in the liquid phase and can be recirculated to the formic acid source.

WO 2012/000,964 teaches a process for obtaining formic acid by thermal separation of a stream comprising formic acid and a tertiary amine, in which combining tertiary amine and a formic acid source produces a liquid stream comprising formic acid and a tertiary amine in a molar ratio of from 0.5 to 5, from 10 to 100% by weight of the secondary components comprised therein are separated off and formic acid is removed by distillation from the resulting liquid stream in a distillation apparatus at a temperature at the bottom of from 100 to 300° C. and a pressure of from 30 to 3000 hPa, and the bottom output from the distillation apparatus is separated into two liquid phases of which the upper liquid phase is enriched in tertiary amine and is recirculated to the formic acid source and the lower liquid phase is enriched in formic acid and is recirculated to removal of the secondary components and/or to the distillation apparatus.

EP application No. 11 194 619.0 teaches an improved process for obtaining formic acid by thermal separation of a stream comprising formic acid and a tertiary amine, in which a liquid stream comprising formic acid, tertiary amine and water is produced by combining tertiary amine and a formic acid source in the presence of water, water and organic degradation products of the tertiary amine are removed and formic acid is distilled from the resulting liquid stream in a distillation apparatus, where the stream comprising water and organic degradation products of the tertiary amine which has been separated off is separated into two liquid phases, the upper liquid phase is removed and the lower, water-comprising liquid phase is recirculated to the formic acid source. The process described in EP application No. 11 194 619.0 allows the relatively simple removal and discharge of various volatile by-products and degradation products of the tertiary amine.

EP application No. 11 194 607.5 teaches an improved process for obtaining formic acid by thermal separation of a stream comprising formic acid and a tertiary amine, in which a liquid stream comprising formic acid and tertiary amine is produced by combining tertiary amine and a formic acid source, secondary components comprised therein are separated off, formic acid is distilled off from the resulting liquid stream in a distillation apparatus, the bottom output from the distillation apparatus is separated into two liquid phases and the upper liquid phase is recirculated to the formic acid source and the lower liquid phase is recirculated to the removal of secondary components and/or the distillation apparatus, where low boilers are separated off by distillation from the upper liquid phase and the depleted stream is recirculated. The process described in EP application No. 11 194 607.5 allows the relatively simple removal and discharge of various volatile by-products and degradation products of the tertiary amine.

It is an object of the present invention to discover an improved process for obtaining formic acid by thermal separation of a stream comprising formic acid and a tertiary amine, which process has advantages over the prior art and is able to give formic acid in high yield and high concentration. In particular, the improved process should also function stably over long operating times and produce formic acid in constant high purity. The process should naturally be able to be carried out very simply and with a very low energy consumption.

BRIEF SUMMARY OF THE INVENTION

We have surprisingly found a process for obtaining formic acid by thermal separation of a stream comprising formic acid and a tertiary amine (I) which at a pressure of 1013 hPa abs has a boiling point which is at least 5° C. higher than that of formic acid, in which a liquid stream comprising formic acid, methanol, water and tertiary amine (I) is produced by combining methyl formate, water and tertiary amine (I) and from 10 to 100% by weight of the methanol comprised therein are separated off from the liquid stream obtained from step (a) and formic acid is removed by distillation from the liquid stream comprising formic acid, water and tertiary amine (I) obtained from step (b) in a distillation apparatus at a temperature at the bottom of from 100 to 300° C. and a pressure of from 30 to 3000 hPa abs.

wherein, when methyl formate, water and tertiary amine (I) are combined in step a), methyl formate, water and optionally tertiary amine (I) are introduced in step (a1), where the molar ratio of the tertiary amine (I) optionally introduced into step (a1) "n(amine to a1)" to the methyl formate introduced into step (a1) "n(mefo to a1)" is such that $$0 \leq n(\text{amine to a1})/n(\text{mefo to a1}) \leq 0.1,$$

and from 70 to 100% of the hydrolysis equilibrium possible under the prevailing conditions is set at a temperature of from 50 to 200° C. and, in step (a2), tertiary amine (I) is subsequently introduced into the stream obtained in step (a1), where the molar ratio of the tertiary amine (I) introduced in step (a2) into the stream obtained in step (a1) "n(amine to a2)" to the methyl formate introduced into step (a1) "n(mefo to a1)" is such that $$0.1 \leq n(\text{amine to a2})/n(\text{mefo to a1}) \leq 2,$$

and the resulting mixture is reacted at a temperature of from 50 to 200° C. so as to give the liquid stream comprising formic acid, methanol, water and tertiary amine (I) mentioned under (a), where the molar ratio of the total tertiary amine (I) introduced into step (a) "n(amine to a)" to the total methyl formate introduced into step (a) "n(mefo to a)" is at least 0.1.

DETAILED DESCRIPTION OF THE INVENTION

Figure 1:
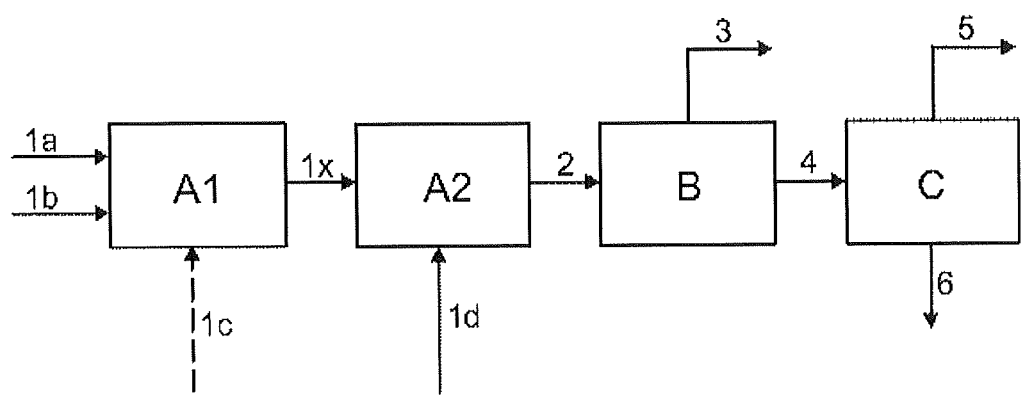
FIG. 1 shows a simplified block diagram of a general embodiment of the process of the invention.

The tertiary amine (I) used in step (a) of the process of the invention has, at a pressure of 1013 hPa abs, a boiling point which is at least 5° C. higher than that of formic acid. The tertiary amine (I) to be used preferably has a boiling point which is at least 10° C. higher, particularly preferably at least 50° C. higher and very particularly preferably at least 100° C. higher, than that of formic acid. In a preferred alternative embodiment of the process of the invention, the tertiary amine (I) to be used has, at a pressure of 1013 hPa abs, an absolute boiling point of at least 111° C., of at best 151° C. in a very preferred alternative embodiment and of at least 201° C. in a most preferred alternative embodiment. A restriction in respect of an upper limit value for the boiling point is not necessary since a very low vapor pressure of the tertiary amine (I) is basically advantageous for the process of the invention. In general, the boiling point of the tertiary amine (I) is below 500° C. at a pressure optionally extrapolated by known methods from vacuum to 1013 hPa abs.

The methyl formate to be used in the process of the invention is generally introduced in liquid form. The methyl formate to be used can come from various sources. The industrially most important source for the synthesis of methyl formate at present is carbonylation of methanol. In addition, recirculated methyl formate which has not been reacted in the hydrolysis and has been separated off in a subsequent step, for example, can also be used in the process of the invention.

The water to be used in the process of the invention is generally likewise introduced in liquid form. To avoid gradual salting-up of the apparatus, preference is given to using demineralized or deionized water.

According to the invention, it has surprisingly been found that tertiary amines (I) tend to be methylated in the presence of methyl formate to form the corresponding methylammonium formate and this effect has a negative influence even under the reaction conditions usual in the prior art in the production of formic acid by hydrolysis of methyl formate in the presence of a tertiary amine, especially during a relatively long running time of a number of weeks or months. In the case of a tertiary amine (I) having three identical radicals R, for example $C_5$-$C_8$-alkyl, the methylation reaction mentioned would be, for example, as follows, where Me is methyl:

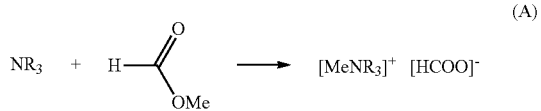

(A)

The methylammonium formate formed can in turn be redissociated, with the starting amine $NR_3$ being obtained back again in a reaction which is the reverse of the reaction equation (A) and a tertiary amine having a methyl group and alkyl formate being formed in another reaction shown in reaction equation (B).

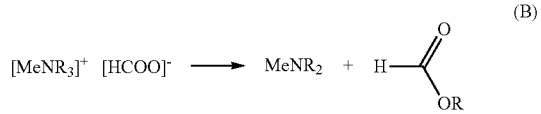

(B)

Furthermore, it has been found in the context of the invention that the tertiary amine comprising a methyl group which is formed according to reaction equation (B) tends to be, in a manner analogous to reaction equations (A) and (B), to be further methylated by methyl formate and dissociated. In this way, the tertiary amine originally used can be successively dissociated through to trimethylamine.

Organic degradation products of the tertiary amine (I) are thus obtained via the reactions mentioned. For the purposes of the present invention, the term "organic degradation products of the tertiary amine (I)" refers generally to compounds which are formed by chemical transformation of the tertiary amine (I) with breaking of bonds originally present, reformation of nitrogen-carbon bonds or chemical transformation of the radicals bound to the nitrogen and any eliminated radicals.

Organic degradation products of the tertiary amine (I) can lead to contamination of the formic acid to be obtained according to step (c). In addition, organic degradation products of the tertiary amine (I) having a boiling point in the range from that of formic acid to that of the tertiary amine (I) tend to accumulate in the distillation apparatus used in step (c) and thereby increase the energy consumption in the distillation apparatus. Organic degradation products of the tertiary amine (I) which do not accumulate in the formic acid to be isolated so as to reduce its purity would have to be discharged at other places in the process in order to prevent uncontrolled accumulation.

The EP application No. 11 194 619.0 mentioned above does relate to the targeted discharge of particular organic degradation products of the tertiary amine (I) but only those which can be separated off together with water in step (b) under the prevailing process conditions. Since the separation according to the teaching of EP application No. 11 194 619.0 is preferably carried out by distillation, this also preferably concerns only those degradation products which can be separated off from the remaining stream by distillation by the gas phase and subsequent condensation.

EP application No. 11 194 607.5 also describes the targeted discharge of particular organic degradation products of the tertiary amine (I). In the case of this discharge, too, the degradation products are separated off by distillation via the gas phase and subsequent condensation, albeit from a different stream and at a different point than in EP application No. 11 194 619.0.

Apart from the problems of possible contamination of the formic acid to be obtained and the discharge of organic degradation products of the tertiary amine (I), the degradation of the tertiary amine (I) naturally also leads to a loss of tertiary amine (I), with the consequence that further amounts of this continually have to be introduced. In order to prevent this, therefore, a smaller loss of tertiary amine (I) would be economically advantageous.

In addition, it has also surprisingly been found in the context of the invention that quaternary methylammonium formates as are formed, for example, by reaction equation (A) catalyze the decomposition of formic acid into carbon dioxide and hydrogen under the customary process conditions of the hydrolysis of methyl formate and the subsequent work-up of the reaction mixture.

It has now surprisingly been found, according to the invention, that the degradation of the tertiary amine (I) to form the organic degradation products of the tertiary amine (I) and in particular the methylation of the tertiary amine (I) by methyl formate to form methylammonium formate (as shown by way of example in reaction equation (A)) can be significantly reduced if, when methyl formate, water and tertiary amine (I) are combined in step (a), (a1) methyl formate, water and optionally tertiary amine (I) are introduced in step (a1), where the molar ratio of the tertiary amine (I) optionally introduced into step (a1) "n(amine to a1)" to the methyl formate introduced into step (a1) "n(mefo to a1)" is such that $$0 \leq n(\text{amine to a1})/n(\text{mefo to a1}) \leq 0.1,$$

and from 70 to 100% of the hydrolysis equilibrium possible under the prevailing conditions is set at a temperature of from 50 to 200° C. and, (a2) in step (a2), tertiary amine (I) is subsequently introduced into the stream obtained in step (a1), where the molar ratio of the tertiary amine (I) introduced in step (a2) into the stream obtained in step (a1) "n(amine to a2)" to the methyl formate introduced into step (a1) "n(mefo to a1)" is such that $$0.1 \leq n(\text{amine to a2})/n(\text{mefo to a1}) \leq 2,$$

and the resulting mixture is reacted at a temperature of from 50 to 200° C. so as to give the liquid stream comprising formic acid, methanol, water and tertiary amine (I) mentioned under (a), where the molar ratio of the total tertiary amine (I) introduced into step (a) "n(amine to a)" to the total methyl formate introduced into step (a) "n(mefo to a)" is at least 0.1.

The methylation of the tertiary amine (I) to methylammonium formate can be effectively reduced by the abovementioned measures according to the invention, which leads not only to a reduction in the concentration of methylammonium formate in the process but also to a reduction in the subsequent reactions, for example the subsequent reaction represented by reaction equation (B).

As reaction apparatuses for the reaction according to the invention of methyl formate, water and tertiary amine (I), it is possible to use all apparatuses which are suitable in principle for this type of reaction. These are generally known to those skilled in the art. They comprise, for example, inter alia, stirred vessels, cascades of stirred vessels, flow reactors, tube reactors, microreactors and residence vessels, in each case with or without direct cooling and with or without further internals. The two steps (a1) and (a2) can, depending on the embodiment, be carried out in a single reactor or in two or more reactors connected in series. If the two steps (a1) and (a2) are carried out in a single reactor, it is generally advantageous to counter backmixing. In the case of a flow reactor, sufficiently low backmixing is often present as a result of the ratio of the flow to the internal cross section, so that it is possible for no further internals to be required here. In the case of a tube reactor, orifice plates or a meandering flow path, for example, may effectively prevent backmixing.

The ratio of the volume available for the reaction in step (a1) to the volume available for the reaction in step (a2) is generally from 0.01 to 10 in the process of the invention. For the purposes of the present invention, the term volume refers to the actual empty volume. The volume of possible internals, for example, is therefore not counted as part of the actual empty volume. The abovementioned volume ratio is preferably from 0.05 to 5, particularly preferably from 0.08 to 2, very particularly preferably from 0.1 to 1 and in particular from 0.15 to 0.9.

The methyl formate, water and tertiary amine (I) to be introduced in step (a1) and (a2) can in each case come from one or more sources. Possible sources are, for example, the introduction of fresh starting material from outside the process or the introduction of recycle streams from the process itself. The individual feed streams to steps (a1) and (a2) can, for example, be introduced separately, previously partially mixed or completely mixed.

Step (a1) will be described in more detail below.

In the process of the invention, the molar ratio of the tertiary amine (I) optionally introduced into step (a1) "n(amine to a1)" to the methyl formate introduced into step (a1) "n(mefo to a1)" is such that $$0 \leq n(\text{amine to a1})/n(\text{mefo to a1}) \leq 0.1,$$

where the mathematical formulation corresponds to a range for the molar ratio in question of from 0 to 0.1. The molar ratio n(amine to a1)/n(mefo to a1) is preferably from 0 to 0.05, particularly preferably from 0 to 0.02 and very particularly preferably from 0 to 0.01. The smaller the molar ratio of the tertiary amine (I) optionally introduced to the methyl formate introduced in step (a1), the smaller is, generally, the formation of undesirable organic degradation products of the tertiary amine (I) under otherwise identical conditions. The introduction of the tertiary amine (I) into step (a1) can therefore even be omitted, which corresponds to a molar ratio of n(amine to a1)/n(mefo to a1) of 0 and also expressed by the "optionally" in the wording of the description of step (a1).

The amount of water which is to be introduced into step (a1) in the process of the invention is advantageously set so that, firstly, the reaction mixture is not diluted too greatly, which would otherwise make the further work-up more difficult owing to the high dilution and large volume streams, and, secondly, a sufficiently high conversion to methyl formate also takes place. In general, a molar ratio of water to methyl formate, calculated from the water introduced into step (a1) "n(water to a1)" to the methyl formate introduced into step (a1) "n(mefo to a1)", of from 0.1 to 10 appears to be advantageous. The molar ratio mentioned is preferably $\geq 0.2$ and particularly preferably $\geq 0.3$, and preferably $\leq 8$ and particularly preferably $\leq 6$.

In step (a1) of the process of the invention, from 70 to 100% of the possible hydrolysis equilibrium under the prevailing conditions is set. Parameters which influence the hydrolysis equilibrium are, for example, the prevailing concentrations of formic acid, methanol, water, methyl formate, and, if introduced into step (a1), also the tertiary amine (I) and naturally also the temperature and the prevailing pressure. For the purposes of the present invention, the hydrolysis equilibrium is the dimensionless K value according to the equation (D)

$$K=[c(\text{formic acid})\cdot c(\text{methanol})]/[c(\text{methyl formate})\cdot c(\text{water})] \qquad (D),$$

where c( . . . ) is in each case the prevailing concentration in mol per liter. Equation (D) applies regardless of whether or not tertiary amine (I) is present in step (a1) and regardless of whether the four components mentioned are present in free form, in ionic form (for example as formate anion HCOO— instead of formic acid HCOOH) or in complexed form. Thus, for example, "c(formic acid)" also comprises the concentration of any formate anion HCOO— present. The percentages mentioned then correspond to the proportion of the maximum K value which is theoretically possible under the prevailing conditions.

In step (a1), preference is given to setting $\geq 75\%$, particularly preferably $\geq 80\%$, very particularly preferably $\geq 85\%$ and in particular $\geq 90\%$, of the hydrolysis equilibrium possible under the prevailing conditions.

The setting of the hydrolysis equilibrium in step (a1) is, at given ratios of amounts of the starting materials, advantageously effected by setting an appropriate residence time at a particular temperature. For the abovementioned temperature range from 50 to 200° C., an average residence time in the range from 0.01 to 5 hours, preferably from 0.02 to 2 hours and particularly preferably from 0.05 to 1 hour, has been found to be advantageous. The higher the temperature, the more quickly can the setting of the hydrolysis equilibrium generally be and the shorter can the average residence time therefore also be.

The hydrolysis in step (a1) is preferably carried out at a temperature of ≥70° C., particularly preferably ≥80° C. and very particularly preferably ≥90° C., and preferably ≤150° C., particularly preferably ≤140° C. and very particularly preferably ≤130° C. The hydrolysis in step (a1) is generally carried out at a temperature of from 70 to 150° C. It has been found that the formation of undesirable organic degradation products of the tertiary amine (I) generally increases with increasing temperature and relatively low temperatures are therefore advantageous in this regard. Furthermore, the corrosion rate increases with temperature, so that relatively low temperatures are also advantageous from this point of view. On the other hand, the reaction rate also decreases with decreasing temperature, so that at very low temperatures the residence time required for a particular conversion increases significantly and uneconomically large reactors would therefore be required. It is advisable to find a compromise between the two effects, which is also reflected in the abovementioned temperature ranges.

The liquid stream obtained from step (a1) is subsequently introduced into step (a2). Step (a2) will therefore be described in more detail below.

In step (a2), tertiary amine (I) is then introduced into the stream obtained in step (a1). In the process of the invention, the molar ratio of the tertiary amine (I) introduced in step (a2) into the stream obtained in step (a1) "n(amine to a2)" to the methyl formate introduced into step (a1) "n(mefo to a1)" is such that $$0 \leq n(\text{amine to a2})/n(\text{mefo to a1}) \leq 2,$$

wherein the mathematical formulation corresponds to a range for the abovementioned molar ratio of from 0.1 to 2. The molar ratio n(amine to a2)/n(mefo to a1) is preferably ≥0.13, particularly preferably ≥0.15 and very particularly preferably ≥0.2, and preferably ≤1.9, particularly preferably ≤1.8 and very particularly preferably ≤1.7, in particular ≤1.5.

In step (a2) of the process of the invention, it is in principle possible to introduce further water and methyl formate in addition to the water and methyl formate already present in the stream from step (a1).

If further water is introduced, the amount thereof is ideally set so that, firstly, the reaction mixture is not diluted too greatly, which would otherwise make the further work-up more difficult because of the high dilution and large volume streams, and, secondly, an advantageous effect of any type results in the further hydrolysis of the methyl formate present or at another point in the further process. Advantageous effects can be, for example, a shift in the equilibrium in the direction of formic acid or an advantageous work-up of the reaction mixture. In general, it is advisable to find a balance between the advantages and disadvantages.

The same applies to the addition of further methyl formates.

The hydrolysis in step (a2) is carried out at a temperature of from 50 to 200° C. It is preferably carried out at a temperature of ≥80° C. and particularly preferably ≥90° C., and preferably ≤170° C. and particularly preferably ≤150° C. The hydrolysis in step (a2) is generally carried out at a temperature of from 70 to 150° C. In step (a2), too, the formation of undesirable organic degradation products of the tertiary amine (I) and the corrosion generally also increases with increasing temperature and relatively low temperatures are advantageous in this regard. On the other hand, the reaction rate also decreases with decreasing temperature, so that at very low temperatures the residence time required for a particular conversion increases significantly and uneconomically large reactors would therefore be required. It is therefore advisable in step (a2), too, to find a compromise between the two effects, which is also reflected in the abovementioned temperature ranges. Accordingly, the temperatures in step (a1) and step (a2) can therefore differ. Within one step, temperature differences as a result of heat evolved in the reaction or active influencing of the temperature by heating or cooling are conceivable and possible.

In step (a2) of the process of the invention, preference is given to setting from 50 to 100% of the hydrolysis equilibrium which is possible under the prevailing conditions, particularly preferably ≥60%, very particularly preferably ≥70% and in particular ≥80%. As mentioned above, the hydrolysis equilibrium is, for example, influenced by the prevailing concentrations of formic acid, methanol, water, methyl formate, and also of tertiary amine (I) since this binds formic acid and naturally also by the temperature and the prevailing pressure. The setting of the hydrolysis equilibrium in step (a2) is, at given ratios of amounts of starting materials, advantageously effected by setting an appropriate residence time at a particular temperature. For the abovementioned temperature range from 50 to 200° C., an average residence time in the range from 0.01 to 5 hours, preferably from 0.2 to 3 hours, particularly preferably from 0.3 to 2 hours, has been found to be advantageous. The higher the temperature, the faster does the setting of the hydrolysis equilibrium generally occur and the shorter can the average residence time accordingly also be.

Furthermore, the molar ratio of the total tertiary amine (I) introduced into step (a) in the process of the invention "n(amine to a)" to the total methyl formate introduced into step (a) "n(mefo to a)" is generally at least 0.1. Here, n(amine to a) corresponds to the sum of all amounts of tertiary amine (I) which are introduced overall into step (a), i.e. the sum of n(amine to a1) and n(amine to a2) in the process divided into steps (a1) and (a2). Correspondingly, n(mefo to a) corresponds to the sum of all amounts of methyl formate which are introduced overall into step (a). In the process divided into steps (a1) and (a2), this therefore corresponds to the sum of n(mefo to a1) and n(mefo to a2), where "n(mefo to a2)" is the amount of methyl formate which is optionally introduced into step (a2) in addition to the stream obtained in step (a1). The molar ratio of n(amine to a)/n(mefo to a) is preferably at least 0.13, particularly preferably at least 0.15 and very particularly preferably at least 0.2.

The upper limit to the molar ratio n(amine to a)/n(mefo to a) is ultimately determined by the sum of the upper limits to the molar ratios n(amine to a1)/n(mefo to a1) and n(amine to a2)/n(mefo to a1) and is therefore redundant as a specific specified number. When n(amine to a1)/n(mefo to a1) is ≤0.1 and n(amine to a2)/n(mefo to a1) is ≤2, the upper limit to n(amine to a)/n(mefo to a) is thus ≤2.1.

The molar ratio of the total water introduced into step (a) "n(water to a)" to the total methyl formate introduced into step (a) "n(mefo to a)" is given by the sum of n(water to a1) and n(water to a2) divided by the sum of n(mefo to a1) and n(mefo to a2). "n(water to a2)" is the amount of the water which is optionally introduced in step (a2) in addition to the stream obtained in step (a1). In general, a molar ratio of n(water to a)/n(mefo to a) of from 0.1 to 10 appears to be advantageous. The abovementioned molar ratio is preferably ≥0.2 and particularly preferably ≥0.3, and preferably ≤8 and particularly preferably ≤6.

The abovementioned measures according to the invention make it possible to achieve a significant reduction in the formation of organic degradation products of the tertiary amine (I).

As discussed in detail above, the combining of methyl formate, water and tertiary amine (I) in step (a) of the process of the invention is carried out in two steps (a1) and (a2). Both steps can in turn be divided into further steps (cascading). These are for the purposes of the present invention referred to collectively as substeps and specifically as steps (a1-i), (a1-ii), (a1-iii) and so forth, or (a2-i), (a2-ii), (a2-iii) and so forth. According to the terminology of the present invention, the steps (a1) and (a2) always comprise the total step (a1) or (a2), regardless of whether these are divided into substeps, can be divided into substeps or are not or cannot be divided into substeps. Substeps make even more finely controlled reaction conditions possible. In particular, it is possible in the individual steps (a1) and (a2) to introduce the individual components methyl formate, tertiary amine (I) and water in a gradated manner. The amounts of components to be introduced in steps (a1) and (a2), for example n(amine to a1) or n(mefo to a1), naturally relate in each case to the sum of any individual additions in the respective step. Likewise, for example, the value of the hydrolysis equilibrium to be set in step (a1) relates to the stream present at the end of step (a1).

Furthermore, it has been found in the context of the present invention that gradated introduction of the tertiary amine (I) into step (a2) in the form of substeps leads to a further reduction in the formation of organic degradation products of the tertiary amine (I). In a preferred variant of the process of the invention, the tertiary amine (I) is therefore introduced in a gradated manner into step (a2). For the purposes of the present invention, a gradated introduction is either a successive or continuous addition along the reaction path. In the context of the process of the invention, the reaction path is the course of the reaction within the respective step, in the present case within step (a2). In the case of successive addition, the amount of tertiary amine (I) to be introduced in step (a2) into the stream obtained in step (a1) is split into a plurality of individual additions along the reaction path. Each individual addition can thus lead to a successive, further reaction of the mixture present. In the limiting case, it is also possible to effect an infinite number of additions of very small amounts of tertiary amine (I), which equates mathematically to continuous addition along the reaction path.

Preference is given to a process according to the invention in which the tertiary amine (I) is introduced in step (a2) into from 2 to 100 substeps, particularly preferably from 2 to 10 substeps, very particularly preferably from 2 to 5 substeps, especially from 2 to 3 substeps and in particular 2 substeps. In principle, the formation of organic degradation products of the tertiary amine (I) can be optimized better in the sense of a further reduction, the more finely stepped the addition of the tertiary amine (I) in step (a2). On the other hand, the outlay both in terms of apparatus and in terms of instrumentation generally also increases with an increase in the number of substeps. In practice, it is therefore advisable to balance the advantages and disadvantages.

If the tertiary amine (I) is introduced in a gradated manner into step (a2) in the process of the invention, it is generally advantageous in terms of a further reduction in the formation of organic degradation products of the tertiary amine (I) to introduce not more than 90% of the total amount of the stream n(amine to a2) in one substep. The remaining amount of the tertiary amine (I) is then distributed over the other substep or steps in step (a2). Preference is given to not more than 80%, particularly preferably not more than 70%, very particularly preferably not more than 60% and in particular not more than 50%, of the total amount of the stream n(amine to a2) being introduced in one substep.

In a preferred variant in which, firstly, the outlay in terms of apparatus and in instrumentation is kept very low by gradated introduction of tertiary amine (I) into step (a2) but, secondly, the formation of organic degradation products of the tertiary amine (I) is noticeably reduced further, from 10 to 90%, particularly preferably from 20 to 80%, very particularly preferably from 30 to 70%, is introduced in one substep of step (a2) and from 10 to 90%, particularly preferably from 20 to 80% and very particularly preferably from 30 to 70%, of the total amount of the stream n(amine to a2) is introduced in a subsequent substep, with from 50 to 100% of the hydrolysis equilibrium possible under the prevailing conditions being set before the subsequent substep. Such a mode of operation firstly generally keeps the specific concentration of tertiary amine (I) prevailing at the respective point of addition based on the concentration of methyl formate at a prescribed amount n(amine to a2) low enough for the formation of organic degradation products of the tertiary amine (I) to be effectively reduced further but on the other hand high enough to bring about further, appreciable hydrolysis of the methyl formate. To utilize this effect to its maximum, from 50 to 100%, preferably ≥60%, particularly preferably ≥70%, very particularly preferably ≥80% and in particular ≥90%, of the hydrolysis equilibrium possible under the prevailing conditions is set before the subsequent substep.

The statements made above regarding the reaction apparatuses also apply in principle to a gradated addition of individual components in one or both of the steps (a1) and/or (a2). Thus, a gradation can, depending on the embodiment, also be carried out in a single reactor or in two or more successive reactors. Correspondingly, it is generally also advantageous to counter backmixing when the reaction is carried out in a single reactor. The statements made with regard to a flow reactor and tube reactor apply analogously. In the case of gradation, a tube reactor with orifice plates is preferably used in the process of the invention.

In the sequence of the individual reaction zones, it may also be advantageous to insert residence zones, i.e. regions in which the reaction mixture has time to react further in the direction of the equilibrium without direct addition of further components in this zone. Thus, for example, it has been found to be useful to divide step (a1) into two substeps, with methyl formate, water and optionally tertiary amine (I) being introduced into the first substep (a1-i) and part of the hydrolysis occurring there and the mixture subsequently being given further time to approach equilibrium in a second substep (a1-ii) without addition of further components.

In a particularly preferred variant, the two steps (a1) and (a2) including possible substeps are carried out in a single tube reactor provided with orifice plates.

In the case of gradated introduction of tertiary amine (I) into step (a2), the volume ratio of the individual substeps depends, inter alia, on the amount of amine introduced in each case, the desired residence time, the desired MeFo conversion and the technically possible mixing times. In general, an attempt will be made to match the volume ratio to the amine ratio. However, a volume distribution independent of the amine ratio is also possible and even advantageous under some circumstances.

Since the reaction of methyl formate with water proceeds exothermically in the presence of a tertiary amine (I), the reaction mixture would accordingly heat up. However, to make a controlled reaction possible, it is advantageous to regulate the temperature profile in the two steps (a1) and (a2) or in any substeps thereof. Possible measures for this purpose are, for example, direct cooling of the respective inflowing stream or the respective inflowing streams or direct cooling in the reactors or the corresponding sections, for example by means of heat exchangers such as cooling coils. A further possibility is, for example, the introduction of tertiary amine (I) having an appropriate temperature into step (a2) or the substeps thereof. The temperature of the tertiary amine (I) can be controlled by, for example, targeted mixing-in of a colder (possibly precooled) or warmer (possibly preheated) stream according to conventional methods of regulation.

The advantage of the present invention over the prior art (no gradation) is a significantly reduced concentration of organic degradation products of the tertiary amine in the hydrolysis output. Thus, the concentration of organic degradation products of the amine in the hydrolysis output can be reduced by 10-100%. The reduction is preferably >20%, particularly preferably >30% and very particularly preferably >50%. Usually, up to 99%, advantageously up to 99.5%, more advantageously up to 99.9% and, in the utmost best cases even up to 100%, of the amount of organic degradation products of the amine are reduced in the hydrolysis output.

The liquid stream produced on combining methyl formate, water and tertiary amine (I) in step (a) generally has a molar ratio of formic acid to tertiary amine (I) of from 0.1 to 10. The molar ratio is preferably ≥0.5 and particularly preferably ≥1, and also preferably ≤5 and particularly preferably ≤3. The molar ratio mentioned is based on the total liquid stream, regardless of whether it is present as a single phase or a plurality of phases.

The liquid stream comprising formic acid and tertiary amine (I) which is produced in step (a) generally has a concentration of formic acid plus tertiary amine (I) of from 1 to 99% by weight, based on the total amount of the stream. The stream mentioned preferably has a concentration of formic acid plus tertiary amine (I) of ≥5% by weight and particularly preferably ≥15% by weight. Even when particularly high concentrations of formic acid plus tertiary amine (I) in the liquid stream produced in step (a) are desirable for the further purification and isolation of the formic acid, the outlay in terms of apparatus and process engineering required to ensure these high concentrations in step (a) also increases. For this reason, the abovementioned concentrations are advantageously ≤90% by weight in the process of the invention. From 10 to 100% by weight of the methanol present in the liquid stream obtained from step (a) are separated off from this liquid stream. The concentration of methanol in the liquid stream produced in step (a) will hereinafter be referred to as "$c_{methanol}$ (stream from step (a))". The liquid stream depleted in methanol corresponds to the stream which is fed to the distillation apparatus as per step (c). This concentration will hereinafter be referred to as "$c_{methanol}$ (feed stream to step (c))". The abovementioned removal of methanol is thus based on the quotient $$1 - \frac{C_{methanol} \text{ (feed stream to step } (c))[g/l]}{C_{methanol} \text{ (stream from step } (a))[g/l]} \cdot 100\% \text{ by weight}$$

Preference is given to ≥20% by weight and particularly preferably ≥30% by weight of the methanol being separated off in step (b). Usually up to ≤99.9% by weight and advantageously ≤99.99% by weight of the methanol are separated off.

The way in which the methanol is separated off is inconsequential for the process of the invention. Thus, for example, the customary and known methods for the separation of liquid mixtures can be used. Separation by distillation may be mentioned first and foremost and is preferred. In this, the liquid mixture is separated in a distillation apparatus.

Apart from methanol, unreacted methyl formate and also further secondary components are naturally also present in the stream from step (a). Here, the term secondary components generally refers to all components which are comprised in the liquid stream obtained in step (a) and are neither formic acid nor tertiary amine (I). Examples which may be mentioned are water, methanol, methyl formate, possible organic degradation products of the tertiary amine (I), dissolved inert gases, and also other components.

It is generally advantageous, in addition to methanol, to also separate off other secondary components, in particular, methyl formate, but also water from the stream from step (a). For the separation of the other secondary components, it is also generally possible to use the customary and known methods for the separation of liquid mixtures. Particular mention may likewise be made of separation by distillation, with it also being possible, depending on the positions of the boiling points, for some of this separation to be performed together in a distillation apparatus. Thus, for example, methanol and other low-boiling secondary components such as methyl formate can be separated off at the top or as a side offtake stream. However, it is also conceivable to separate off high-boiling secondary components at the bottom and the mixture comprising formic acid and tertiary amine (I) as side stream or even as overhead product. Apart from separation by distillation, membrane, absorption, adsorption, crystallization, precipitation, filtration, sedimentation or extraction processes are also possible. A combination of a plurality of separation processes is also possible.

It is naturally also possible to combine a plurality of separation steps which may also be based on different methods. The design of the separation step or separation steps can be undertaken using conventional technical knowledge.

The main critical factor for the order of the removal of methanol and further secondary components by distillation is the position of the boiling points. Thus, it is particularly advantageous firstly to separate off methyl formate at the top of a first distillation apparatus. This can then preferably be recirculated to step (a), with the yield of formic acid based on the methyl formate used being able to be increased significantly thereby. Methanol is advantageously taken off as side offtake stream from the same distillation apparatus. However, as an alternative, it is also possible to separate off methanol in a separation distillation apparatus. The methanol which has been separated can, for example, be reused in the synthesis of methyl formate. In a subsequent distillation apparatus, water and any further secondary components which can be separated off together with water by distillation can then advantageously be removed via the top. The water which has been separated off can also be recirculated to step (a). Since small amounts of secondary components are still comprised in the water which has been separated off, the recirculation avoids specific disposal of the water which has been separated off. The bottom product obtained after the removal of water and any further secondary components in this particularly advantageous variant comprises formic acid, residual water and tertiary amine (I). According to the invention, this can then be passed to step (c).

If water is separated off in addition to methanol in step (b) of the process of the invention, the amount of water separated off is generally from 10 to 100% of the amount of water comprised in the stream from step (a). Preference is given to ≥20% and particularly preferably ≥30% and preferably ≤97% and particularly preferably ≤95% of the amount of water comprised in the stream from step (a) being separated off in step (b).

Although the formation of organic degradation products of the tertiary amine (I) is significantly reduced by the measures according to the invention for reducing the formation of organic degradation products of the tertiary amine (I), it is not completely prevented. It is therefore also advantageous in the process of the invention to separate off the organic degradation products of the tertiary amine (I) removed together with the water according to the teaching of EP application No. 11 194 619.0 and discharge them from the process. For this purpose, the stream comprising water and organic degradation products of the tertiary amine which has been separated off in step (b) is separated into two liquid phases, the upper liquid phase comprising the organic degradation products of the tertiary amine (I) is removed and the lower, water-comprising liquid phase is recirculated to step (a).

Of course, further process steps apart from step (b) can be carried out between steps (a) and (c) in the process of the invention.

Finally, formic acid is removed by distillation in a distillation apparatus at a temperature at the bottom of from 100 to 300° C. and a pressure of from 30 to 3000 hPa abs from the liquid stream obtained from step (b). As distillation apparatuses for this purpose, it is in principle possible to use the apparatuses known to those skilled in the art for such separation tasks or can be designed by a person skilled in the art using general technical knowledge.

The distillation apparatus usually comprises not only the actual column body with internals but also, inter alia, an overhead condenser and a bottom vaporizer. In addition, these can naturally also comprise further peripheral apparatuses or internals, for example a flash vessel in the feed line (for example to separate gas and liquid in the feed to the column body), an intermediate vaporizer (for example for improved heat integration of the process) or internals for avoiding or reducing aerosol formation (for example heatable trays, demisters, coalescers or deep-bed diffusion filters). The column body can be equipped, for example, with ordered packing, random packing elements or trays. The number of theoretical plates required is dependent, in particular, on the type of tertiary amine (I), the concentration of formic acid and tertiary amine (I) in the feed to the distillation apparatus in step (c) and the desired concentration or the desired purity of the formic acid, and can be determined in a conventional way by a person skilled in the art. The number of theoretical plates required is generally ≥3, preferably ≥6 and particularly preferably ≥7. There are in principle no upper limits. However, for practical reasons it will be usual to use generally ≤70, optionally ≤50, theoretical plates or even ≤30 theoretical plates.

The stream comprising formic acid and tertiary amine (I) from step (b) can be fed, for example, as side stream to the column body in the distillation apparatus.

A flash evaporator, for example, can optionally also precede the addition. To keep the thermal stress on the stream fed into the distillation apparatus as small as possible, it is generally advantageous to feed this in in a relatively low region of the distillation apparatus. Thus, in step (c), the stream comprising formic acid and tertiary amine (I) is preferably fed in in the region of the lower quarter, preferably in the region of the lower fifth and particularly preferably in the region of the lower sixth, of the theoretical plates present, with direct introduction into the bottom naturally also being comprised here.

As an alternative, preference is also given, in step (c), to feed said stream comprising formic acid and a tertiary amine (I) from step (b) into the bottom vaporizer of the distillation apparatus.

The distillation apparatus is operated at a temperature at the bottom of from 100 to 300° C. and a pressure of from 30 to 3000 hPa abs. The distillation apparatus is preferably operated at a temperature at the bottom of ≥120° C., particularly preferably ≥140° C., and preferably ≤220° C. and particularly preferably ≤200° C. The pressure is preferably ≥30 hPa abs, particularly preferably ≥60 hPa abs, and preferably ≤1500 hPa abs and particularly preferably ≤500 hPa abs.

Depending on the composition of the feed comprising formic acid and tertiary amine (I) to the distillation apparatus, formic acid can be obtained as overhead product and/or side product from the distillation apparatus. If the feed comprises constituents having boiling points lower than that of formic acid, it may be advantageous to separate these off as overhead product and separate off the formic acid at a side offtake in the distillation. In the case of possible dissolved gases in the feed, it is generally also possible to separate off the formic acid together with these as overhead product. If the feed comprises constituents having boiling points higher than that of formic acid, formic acid is preferably separated off by distillation as overhead product, but optionally instead or additionally in the form of a second stream at the side offtake. The constituents which have boiling points higher than that of formic acid are in this case preferably taken off in an additional side stream. The side stream comprising secondary components can optionally be recirculated to step (b) in order to separate off the secondary components.

Formic acid having a content of up to 100% by weight can be obtained in this way. In general, formic acid contents of from 75 to 99.995% by weight can be achieved without problems. The balance to 100% by weight is mainly water, with other components such as possible decomposition products naturally also being conceivable as materials apart from formic acid and the tertiary amine (I) introduced into the distillation apparatus.

In the isolation of concentrated formic acid having a content of from 95 to 100% by weight as overhead or side product, water is discharged in a side stream together with part of the formic acid split off. The formic acid content of the side stream is typically from 75 to 95% by weight. The aqueous formic acid in the side stream can optionally be recirculated to step (b) or to any point in the process in order to separate off the water.

However, it is also possible to discharge the water and the formic acid split off in a joint overhead or side stream. The formic acid content of the product obtained in this way is then generally from 85 to 95% by weight.

To largely suppress, in particular, the formation of organic decomposition products of the tertiary amine (I), which are formed by oxidation, it is particularly advantageous, especially when the distillation apparatus is operated at pressures below 0.1 MPa abs, for the intrusion of oxygen through a large number of connections, ports and flanges to be avoided or at least kept extremely low by special care during installation, by use of particularly well-sealed flange connections (for instance those having comb profile seals or weld lip seals) or by means of nitrogen-blanketed flange connections. A suitable flange connection is disclosed, for example, in DE 10 2009 046 310 A1.

The formic acid which can be obtained by the process of the invention has a low color number and also a high color number stability. In general, a color number of ≤20 APHA, in particular even ≤10 APHA and possibly even ≤5 APHA, can be achieved without problems. Even on storage for a number of weeks, the color number remains virtually constant or increases only insignificantly.

Owing to the measures according to the invention, a particularly pure formic acid in which the organic decomposition products of the tertiary amine (I) are generally present in a concentration of ≤70 ppm by weight, preferably ≤30 ppm by weight and very particularly preferably ≤20 ppm by weight, can be obtained without a further outlay.

In addition, the overall content of secondary components (i.e. inclusive of the organic decomposition products of the tertiary amine (I)) is extremely low and is generally ≤100 ppm by weight, preferably ≤50 ppm by weight and very particularly preferably ≤25 ppm by weight.

It may also be advantageous to use a plurality of distillation apparatuses in step (c), particularly when further fractions, for example accompanying materials comprised, reaction by-products, impurities and/or formic acid fractions of various purities and concentrations, are to be obtained in addition to the free formic acid and the amine (I)-comprising bottom product.

The distillation apparatus for separating off the formic acid can naturally also be configured as thermally coupled distillation columns or as a dividing wall column.

In a preferred form of the process of the invention, the tertiary amine (I) to be used in step (a) and the degree of separation in the distillation apparatus mentioned in step (c) are selected so that two liquid phases are formed in the bottom output from the distillation apparatus mentioned in step (c), (d) the bottom output from the distillation apparatus mentioned in step (c) is separated into two liquid phases, where the upper liquid phase has a molar ratio of formic acid to tertiary amine (I) of from 0 to 0.5 and the lower liquid phase has a molar ratio of formic acid to tertiary amine (I) of from 0.5 to 5;

(e) the upper liquid phase from the phase separation in step (d) is recirculated to step (a); and (f) the lower liquid phase from the phase separation in step (d) is recirculated to step (b) and/or (c).

The formation of two liquid phases is determined mainly by the chemical and physical properties of the two phases. These can in turn be influenced by the choice of the tertiary amine (I) to be used, by the degree of separation in the distillation apparatus and also by the presence of any additional components.

For the present purposes, the degree of separation is the quotient $$\frac{m_{formic\ acid}(\text{feed stream to step }(c))[g/h] - m_{formic\ acid}(\text{bottom output})[g/h]}{m_{formic\ acid}(\text{feed stream to step }(c))[g/h]} \cdot 100\%$$

where "$m_{formic\ acid}$(feed stream to step (c))" is the amount of formic acid fed per unit time to the distillation apparatus and "$m_{formic\ acid}$(bottom output)" corresponds to the amount of formic acid discharged per unit time in the bottom output. In this preferred embodiment of the process of the invention, the degree of separation selected is generally ≥10%, preferably ≥25% and particularly preferably ≥40%, and generally ≤99.9%, preferably ≤99.5% and particularly preferably ≤99.0%. The degree of separation can, for example, be easily influenced by the temperature and pressure conditions in the distillation apparatus and by the residence time in the distillation apparatus. It can be determined by means of simple tests, optionally also during operation of the process of the invention.

The suitability of a tertiary amine (I) can be determined, for example, in simple tests in which the number of phases is determined under the conditions envisaged.

The phase separation can, for example, be carried out in a separate phase separator located downstream of the distillation apparatus. However, it is also possible to integrate the phase separator into the bottom region of the distillation apparatus, in the region of the bottom vaporizer or else in the region of the bottom vaporizer circuit. Here, it is also possible or may even be advantageous to use, for example, a centrifugal separator.

Since the formation of two liquid phases is also influenced by the temperature in addition to the chemical and physical properties of the two phases and the miscibility generally increases with temperature, it may be advantageous to operate the phase separation at a lower temperature than the temperature at the bottom previously selected in order to improve the phase separation. For this purpose, the bottom output is usually cooled to a temperature in the range from 30 to 180° C. in an intermediate heat exchanger. The phase separation is preferably carried out at a temperature of ≥50° C. and at a temperature of ≤160° C. and particularly preferably at a temperature of ≤130° C.

The upper liquid phase in step (d) has a molar ratio of formic acid to tertiary amine (I) in general from 0 to 0.5, preferably ≥0.005 and particularly preferably ≥0.015 and also preferably ≤0.25 and particularly preferably ≤0.125. The lower liquid phase in step (d) has a molar ratio of formic acid to tertiary amine (I) in general from 0.5 to 4, preferably ≥0.75 and particularly preferably ≥1 and also preferably ≤3.5 and particularly preferably ≤3. However, depending on the choice of the amine, it can of course also be possible for the phase comprising formic acid to form the upper phase and the amine phase having a molar formic acid/amine ratio of from 0 to 0.5 to form the lower phase. It is merely important that there is a phase separation with one phase having a molar ratio of formic acid to tertiary amine of in general from 0 to 0.5 and a second phase having a molar ratio of formic acid to tertiary amine of in general from 0.5 to 4. The upper phase is preferably that having a molar ratio of formic acid to tertiary amine of in general from 0 to 0.5 and the lower phase is preferably that having a molar ratio of formic acid to tertiary amine of in general from 0.5 to 4.

Furthermore, it is advantageous in the process of the invention to select the degree of separation of the distillation apparatus mentioned in step (c) in such a way that the molar ratio of formic acid to tertiary amine (I) in the bottom output is from 0.1 to 2.0. For the purposes of the present invention, the bottom output is the totality of the liquid bottom condensates which leave the distillation apparatus and are separated into two liquid phases in step (d). It is inconsequential whether the bottom condensates originate, for example, directly from the bottom of the distillation apparatus, the bottom of the bottom vaporizer or from both. The degree of separation of the distillation apparatus mentioned in step (c) is preferably selected so that the molar ratio of formic acid to tertiary amine (I) in the bottom output is preferably ≤1.5.

As a result of the preferred recirculation of the upper liquid phase from the phase separation in step (d) to step (a) as per step (e), the tertiary amine (I) comprised in the upper liquid phase can be used, by combination with the formic acid source, for further generation of a stream comprising formic acid and tertiary amine (I). In general, from 10 to 100%, preferably from 50 to 100%, particularly preferably from 80 to 100%, very particularly preferably from 90 to 100% and in particular from 95 to 100%, of the upper liquid phase is recirculated to step (a).

It is of course also possible for further process steps to be integrated into the recirculation of the upper liquid phase. A nonlimiting example which may be mentioned is, for instance, freeing of the upper liquid phase to be recirculated or the tertiary amine (I) comprised therein of undesirable accompanying materials, reaction by-products or impurities. The type of intermediate process steps are in principle not subject to any limits. It is also possible to remove part of the upper liquid phase in a targeted manner as "purge stream". Missing amounts of tertiary amine (I) or amounts of this which have been lost can naturally be replaced again by fresh tertiary amine (I) which, for example, can be introduced via the recycle stream or directly into step (a).

As mentioned above, although the formation of organic degradation products of the tertiary amine (I) is significantly reduced by measures according to the invention for reducing the formation of organic degradation products of the tertiary amine (I), it is not completely prevented. It is therefore advantageous in the process of the invention to separate off the low-boiling, organic degradation products of the tertiary amine (I) which have accumulated in the upper liquid phase from the phase separation in step (d), by distillation according to the teaching of EP application No. 11 194 607.5 before the above-described recirculation of the upper liquid phase and discharge these from the process.

The preferred recirculation of the lower liquid phase from the phase from step (d) to step (b) and/or (c), as per step (f), enables the formic acid comprised in the lower liquid phase likewise to be utilized for isolating formic acid by removal by distillation. Depending on the desired embodiment, the lower liquid phase can thus be recirculated (i) to step (b), (ii) partly to step (b) and partly to (c) or (iii) to step (c). However, preference is generally given to recirculation to step (c) since the stressing of the lower liquid phase comprising formic acid and tertiary amine (I) is usually the lowest in this case and the quantity of the stream in step (b) is not increased, which would otherwise have the consequence of correspondingly larger dimensions. In general, from 10 to 100%, preferably from 50 to 100%, particularly preferably from 80 to 100%, very particularly preferably from 90 to 100% and in particular from 80 to 100%, of the lower liquid phase is recirculated to step (b) and/or (c).

It is of course also possible for further process steps to be integrated into the recirculation of the lower liquid phase. As a nonlimiting example, mention may, here too, be made of a purification of the lower liquid phase to be recirculated or of the tertiary amine (I) comprised therein and/or the formic acid comprised therein in order to remove undesirable accompanying materials, reaction by-products or further impurities. The type of intermediate process steps is also in principle not subject to any limits. It is also possible to discharge part of the lower liquid phase in a targeted manner as "purge stream" in order to remove, for example, undesirable accompanying materials, reaction by-products or further impurities.

It has surprisingly been found in the context of the present invention that quaternary methylammonium formates, as are formed in the formation of organic degradation products of the tertiary amine (I) in the presence of methyl formate, can be partially reconverted into the tertiary amine (I) by the action of heat, e.g. during distillation. A particularly surprising aspect was the fact that the methyl group is preferentially eliminated although statistically this should occur only with a probability of 25%. Thus, for example, methyltri-n-hexylammonium formate is redissociated into tri-n-hexylamine and methyl di-n-hexylamine in a ratio of 1:1 as a result of distillation, and not in the statistically expected ratio of only 1:3.

In a preferred variant of the process of the invention, formic acid and tertiary amine (I) are therefore distilled from the lower liquid phase from the phase separation in step (d) at a temperature at the bottom of from 80 to 300° C. and a pressure of from 1 to 1000 hPa abs in a distillation apparatus in step (g) and the stream which has been distilled off is recirculated to one of the abovementioned steps (a) to (f). The stream which has been distilled off in step (g) is preferably recirculated to step (b).

Possible distillation apparatuses for this purpose are in principle the apparatuses which are known to a person skilled in the art for such separation tasks or can be designed by a person skilled in the art using general technical knowledge. The distillation apparatus is operated at a temperature at the bottom of from 80 to 300° C. and a pressure of from 1 to 1000 hPa abs. The distillation apparatus is preferably operated at a temperature at the bottom of ≥120° C., particularly preferably ≥140° C., and preferably ≤220° C. and particularly preferably ≤200° C. The pressure is preferably ≥5 hPa abs, particularly preferably ≥10 hPa abs, and preferably ≤500 hPa abs and particularly preferably ≤250 hPa abs.

The stream comprising formic acid and tertiary amine (I) which is distilled off is generally obtained as overhead product. However, it is also possible for it to be obtained as side stream especially when relatively low-boiling components are also to be separated off at the same time in the distillation.

In the process of the invention, it is usual to pass from 0.01 to 50% of the lower liquid phase from the phase separation in step (d) to step (g). This amount is sufficient firstly to redissociate the quaternary methylammonium formate to a sufficient extent but secondly also to keep the outlay, for example, the size of the distillation apparatus or the ongoing energy requirement, within bounds. Preference is given to passing ≥0.1% and particularly preferably ≥0.5% and also preferably ≤20%, particularly preferably ≤10% and very particularly preferably ≤5%, of the upper liquid phase from the phase separation in step (d) to step (g).

Thus, part of the organic degradation products of the tertiary amine (I) can even be converted back into valuable tertiary amine (I) by means of step (g).

The tertiary amine (I) which is preferably to be used in the process of the invention has the general formula (Ia)

$$NR^1R^2R^3 \quad (Ia),$$

where the radicals $R^1$ to $R^3$ are identical or different and are each, independently of one another, an unbranched or branched, acyclic or cyclic, aliphatic, araliphatic or aromatic radical having in each case from 1 to 16 carbon atoms, preferably from 1 to 12 carbon atoms, where individual carbon atoms can also be, independently of one another, replaced by a heterogroup selected from the group consisting of —O— and >N— and two or all three radicals can also be joined to one another to form a chain comprising at least four atoms.

Examples of suitable amines are:

Tri-n-propylamine ($bp_{1013\ hPa}=156°$ C.), tri-n-butylamine, tri-n-pentylamine, tri(3-methylbutyl)amine, tri-n-hexylamine, tri-n-heptylamine, tri-n-octylamine, tri-n-nonylamine, tri-n-decylamine, tri-n-undecylamine, tri-n-dodecylamine, tri-n-tridecylamine, tri-n-tetradecylamine, tri-n-pentadecylamine, tri-n-hexadecylamine, tri(2-ethylhexyl)amine, tri(2-propylheptyl)amine.

Dimethyldecylamine, dimethyldodecylamine, dimethyltetradecylamine, ethyl-di(2-propyl)amine ($bp_{1013\ hPa}=127°$ C.), di-n-octylmethylamine, di-n-hexylmethylamine, di-n-hexyl(2-methylpropyl)amine, di-n-hexyl(3-methylbutyl)amine, methyl-di(2-ethylhexyl)amine, di-n-hexyl(1-methyl-n-hexyl)amine, di-2-propyldecylamine.

Tricyclopentylamine, tricyclohexylamine, tricycloheptylamine, tricyclooctylamine and derivatives thereof substituted by one or more methyl, ethyl, 1-propyl, 2-propyl, 1-butyl, 2-butyl or 2-methyl-2-propyl groups.

Dimethylcyclohexylamine, methyldicyclohexylamine, diethylcyclohexylamine, ethyldicyclohexylamine, dimethylcyclopentylamine, methyldicyclopentylamine, methyldicyclohexylamine.

Triphenylamine, methyldiphenylamine, ethyldiphenylamine, propyldiphenylamine, butyldiphenylamine, 2-ethylhexyldiphenylamine, dimethylphenylamine, diethyl-phenylamine, dipropylphenylamine, dibutylphenylamine, bis(2-ethylhexyl)phenyl-amine, tribenzylamine, methyldibenzylamine, ethyldibenzylamine and derivatives thereof substituted by one or more methyl, ethyl, 1-propyl, 2-propyl, 1-butyl, 2-butyl or 2-methyl-2-propyl groups.

1,5-Di(1-piperidyl)pentane, N—$C_1$-$C_{12}$-alkylpiperidines, N,N-di-$C_1$-$C_{12}$-alkyl-piperazines, N—$C_1$-$C_{12}$-alkylpyrrolidines, N—$C_1$-$C_{12}$-alkylimidazoles and derivatives thereof substituted by one or more methyl, ethyl, 1-propyl, 2-propyl, 1-butyl, 2-butyl or 2-methyl-2-propyl groups.

1,8-Diazabicyclo[5.4.0]undec-7-ene ("DBU"), 1,4-diazabicyclo[2.2.2]octane, N-methyl-8-azabicyclo[3.2.]octane ("tropane"), N-methyl-9-azabicyclo[3.3.1]nonane ("granatane"), 1-azabicyclo[2.2.2]octane ("quinuclidine"), 7,15-diazatetracyclo[7.7.1.0$^{2,7}$.0$^{10,15}$]heptadecane ("sparteine").

It is naturally also possible to use mixtures of various tertiary amines (I) in the process of the invention. Naturally, all tertiary amines (I) used then preferably have, at a pressure of 1013 hPa abs, a boiling point which is at least 5° C. higher than that of formic acid.

Among the above-described tertiary amines of the general formula (Ia), preference is in turn given to those in which the radicals $R^1$ to $R^3$ are identical or different and are each, independently of one another, an unbranched or branched, acyclic or cyclic, aliphatic, araliphatic or aromatic radical having in each case from 1 to 16 carbon atoms, preferably from 1 to 12 carbon atoms, where individual carbon atoms may also be, independently of one another, replaced by a heterogroup selected from the group consisting of —O— and >N— and two or all three radicals can also be joined to one another to form a saturated chain comprising at least four atoms.

Preference is given to at least one of the radicals on the alpha-carbon atom, i.e. on the carbon atom bound directly to the amine nitrogen atom, having two hydrogen atoms.

In the process of the invention, particular preference is given to using an amine of the general formula (Ia) in which the radicals $R^1$ to $R^3$ are selected independently from the group consisting of $C_1$-$C_{12}$-alkyl, $C_5$-$C_8$-cycloalkyl, benzyl and phenyl as tertiary amine (I).

Very particular preference is given to using a saturated amine of the general formula (Ia) as tertiary amine (I) in the process of the invention.

In particular, an amine of the general formula (Ia) in which the radicals $R^1$ to $R^3$ are selected independently from the group consisting of $C_5$-$C_8$-alkyl and $C_5$-$C_8$-cycloalkyl, in particular tri-n-pentylamine, tri-n-hexylamine, tri-n-heptylamine, tri-n-octylamine, dimethylcyclohexylamine, methyldicyclohexylamine, dioctylmethylamine and dimethyldecylamine, is used as tertiary amine (I) in the process of the invention. Most specifically, an amine of the general formula (Ia) in which the radicals $R^1$ to $R^3$ are selected independently from the group consisting of $C_5$-$C_8$-alkyl, in particular tri-n-pentylamine, tri-n-hexylamine, tri-n-heptylamine and tri-n-octylamine, is used as tertiary amine (I) in the process of the invention.

In a further embodiment, amines which have a branch on the alpha-carbon atom (the carbon atom bound directly to the amine nitrogen atom), on the beta-carbon atom (the second carbon atom from the amine nitrogen atom) or the gamma-carbon atom (the third carbon atom from the amine nitrogen atom) are used. Here, alkyl, aryl and other substituents are conceivable in principle, with preference being given to alkyl groups such as methyl, ethyl, 1-propyl or 2-propyl, or piperidinyl groups. In this embodiment, particular preference is given to N-ethylpiperidine, tri(3-methylbutyl)amine, di-n-hexyl(2-methylpropyl)amine, di-n-hexyl(3-methylbutyl)amine, methyldi(2-ethylhexyl)amine, di-n-hexyl(1-methyl-n-hexyl)amine, di-2-propyldecylamine, methyldicyclohexylamine, 1,5-di(1-piperidyl)pentane.

The streams comprising formic acid and tertiary amine (I) which are formed in the process of the invention can comprise not only free formic acid and the free tertiary amine (I) but also, in admixture with these, formic acid and the tertiary amine (I) in various other forms. The type and amount of the individual forms can differ as a function of the prevailing conditions, for instance the relative ratio of formic acid to tertiary amine (I), the presence of further components (for example water, by-products, impurities) and thus ultimately also the concentration of formic acid and tertiary amine (I), the temperature and the pressure. Thus, for example, the following conceivable forms may be mentioned:

Ammonium formate (molar ratio of formic acid to tertiary amine (I) of 1) or formic acid-rich adduct with the tertiary amine (I) (molar ratio of formic acid to tertiary amine (I) of >1).

Ionic liquid.

The type and amount of the individual forms is inconsequential for carrying out the process of the invention.

FIG. 1 shows a simplified block diagram of a general embodiment of the process of the invention. In the figure, the individual letters have the following meanings:
- A1=First stage of the apparatus for producing a stream comprising formic acid, tertiary amine (I) and water
- A2=Second stage of the apparatus for producing a stream comprising formic acid, tertiary amine (I) and water
- B=Apparatus for separating off methanol and optionally other secondary components
- C=Distillation apparatus Methyl formate via stream (1a) and water via stream (1b) are fed to the first stage A1 of the apparatus for producing a stream comprising formic acid, tertiary amine (I) and water. According to the invention, a certain amount of tertiary amine (I) can also be introduced via stream (Ic). However, the addition of tertiary amine (I) to A1 can also be omitted. In FIG. 1, this is indicated by a broken-line arrow. At least part of the hydrolysis reaction takes place in A1. The reaction mixture is then fed via stream (1x) from the first stage A1 to the second stage A2 of the apparatus for producing a stream comprising formic acid, tertiary amine (I) and water. The addition of tertiary amine (I) takes place via stream (1d). The stream (2) comprising formic acid, tertiary amine (I) and water is subsequently taken off from the second stage A2 of the abovementioned apparatus and passed to removal of methanol and optionally further secondary components in apparatus B. This is preferably a distillation apparatus. Methanol and any further secondary components which have been separated off are taken off via stream (3). The stream enriched in formic acid and tertiary amine (I) is fed via stream (4) to the distillation apparatus C. In this, formic acid is separated off as stream (5) by distillation. The bottoms from the distillation apparatus C are taken off as stream (6).

If the apparatus B is a preferred distillation apparatus, this can also have, for example, the configurations disclosed in FIG. 12 to 13 of WO 2012/000,964. The distillation apparatus C can, for example, have the configurations disclosed in FIG. 2 to 7 of WO 2012/000,964.

Figure 2:
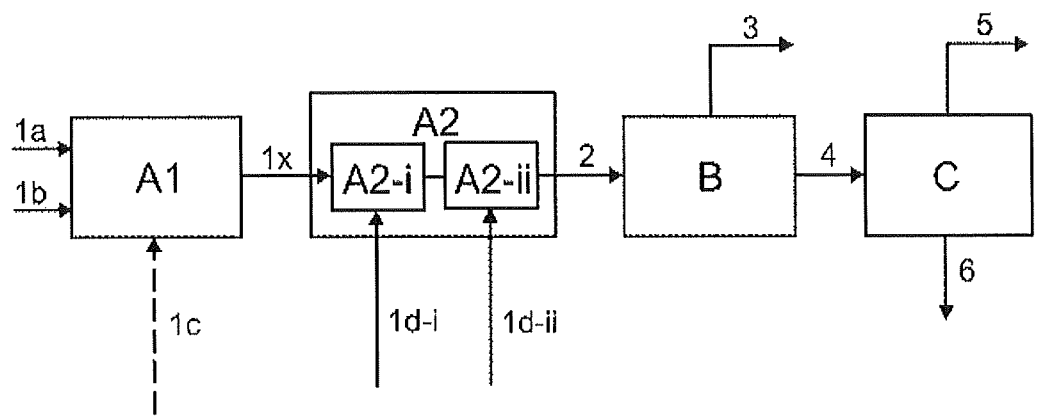
FIG. 2 shows a simplified block diagram of a modified embodiment in which the second stage A2 of the apparatus for producing a stream comprising formic acid, tertiary amine (I) and water is divided into two substages A2-i and A2-ii.

FIG. 2 shows a simplified block diagram of a modified embodiment in which the second stage A2 of the apparatus for producing a stream comprising formic acid, tertiary amine (I) and water is divided into two substages A2-i and A2-ii. Tertiary amine (I) is in each case introduced via streams (1d-i) and (1d-ii). The apparatuses A1, A2, B and C have the meanings indicated in FIG. 1.

Figure 3:
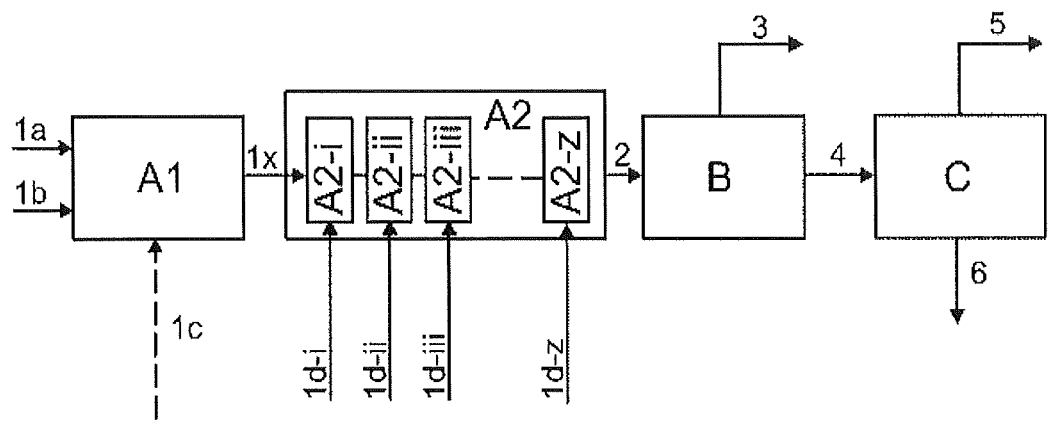
FIG. 3 shows a further simplified block diagram of a modified embodiment in which the second stage A2 of the apparatus for producing a stream comprising formic acid, tertiary amine (I) and water is divided into a theoretically infinite number of substages A2-i, A2-ii, A2-iii to A2-z.

FIG. 3 shows a further simplified block diagram of a modified embodiment in which the second stage A2 of the apparatus for producing a stream comprising formic acid, tertiary amine (I) and water is divided into a theoretically infinite number of substages A2-i, A2-ii, A2-iii to A2-z. Tertiary amine (I) is in each case introduced via the streams (1d-i), (1d-ii), (1d-iii) to (1d-z). The apparatuses A1, A2, B and C likewise have the meanings indicated in FIG. 1.

Figure 4:
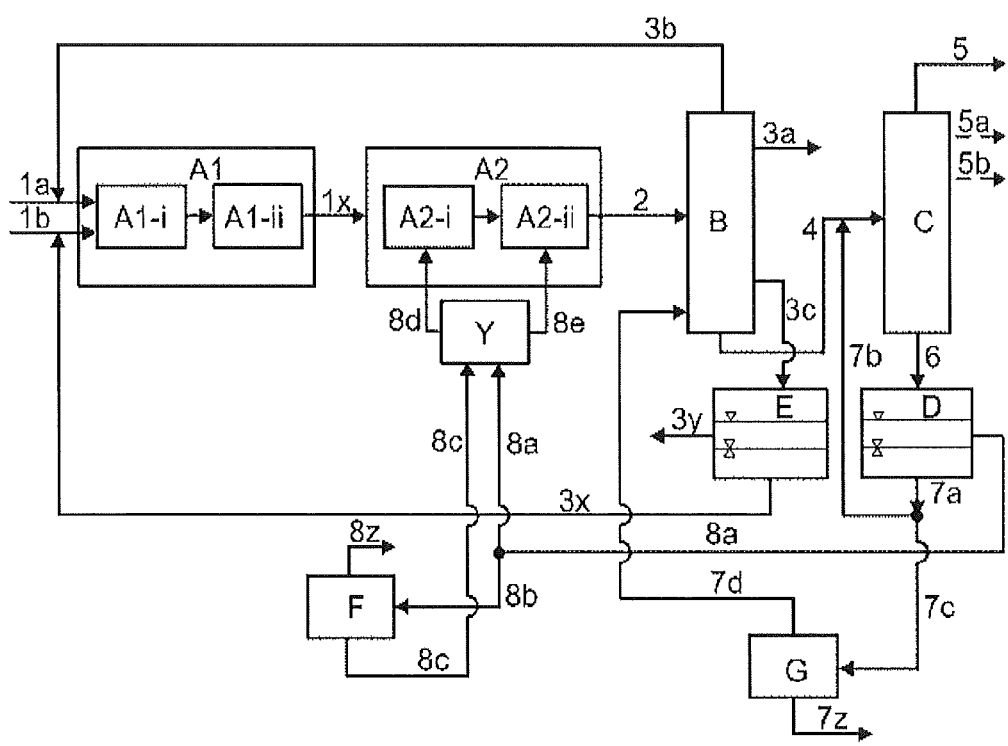
FIG. 4 shows a simplified block diagram of a preferred embodiment for obtaining formic acid by hydrolysis of methyl formate.

A preferred embodiment for obtaining formic acid by hydrolysis of methyl formate is shown in FIG. 4 by means of a simplified block diagram. In the figure, the individual letters have the following meanings:
- A1=first stage of the apparatus for producing a stream comprising formic acid, tertiary amine (I) and water, which comprises the substages A1-i and A1-ii
- A2=second stage of the apparatus for producing a stream comprising formic acid, tertiary amine (I) and water, which comprises the substages A2-i and A2-ii
- B=distillation apparatus for separating off methanol and optionally further secondary components
- C=distillation apparatus for obtaining formic acid
- D=phase separation vessel
- E=phase separation vessel
- F=distillation apparatus for separating off low boilers
- G=distillation apparatus for separating off high boilers and redissociating quaternary methylammonium formats
- Y=metering apparatus Methyl formate (streams (1a) and (3b)) and water (streams (1b) and (3x)) are fed to the first stage A1 of the apparatus for producing a stream comprising formic acid, tertiary amine (I) and water and mixed in substrate A1-i. In this, a not insignificant part of the hydrolysis takes place. The reaction mixture is then fed to substage A1-ii, which first and foremost has the function of a residence vessel and provides the reaction mixture with time for further reaction in the direction of equilibrium. From the residence vessel, the reaction mixture then goes via stream (1x) to the second stage A2 of the apparatus for producing a stream comprising formic acid, tertiary amine (I) and water. This is likewise divided into two substages. In substage A2-i, the first part of the tertiary amine (I) is added via the metering apparatus Y and stream (8d), so that formic acid can react with the tertiary amine (I). In addition, further hydrolysis of methyl formate also takes place. The reaction mixture is then passed on to substage A2-ii into which tertiary amine (I) is likewise introduced via the metering apparatus Y and stream (8e). Further reaction of formic acid with the added tertiary amine (I) and also further hydrolysis of methyl formate take place in substage A2-ii. As apparatus for A1 and A2, it is possible to use, for example, a tube reactor which has orifice plates at the transitions between stages and substages. The temperature in the reactor is advantageously regulated by means of built-in heat exchangers (e.g. cooling coils) and by targeted setting of the temperature of the tertiary amine (I) to be added in A2-i and A2-ii.

The reaction mixture is then taken off as stream (2) from the apparatus A2-ii and fed to the apparatus B. Stream (2) comprises predominantly formic acid, tertiary amine (I), methanol, water and unreacted methyl formate.

In the distillation apparatus B, unreacted methyl formate (stream (3b)), methanol formed in the hydrolysis (stream (3a)) and water and organic decomposition products of the tertiary amine (I) (stream (3c)) are separated off from stream (2). Stream (3b) comprising unreacted methyl formate is recirculated to the apparatus A1. The methanol separated off via stream (3a) can, for example, be reused for preparing methyl formate. Stream (3c) comprising water and organic degradation products of the tertiary amine (I) is fed to the phase separation vessel E and separated into two liquid phases. The lower phase comprising water is recirculated as stream (3x) to the apparatus A1. The upper phase comprising organic degradation products of the tertiary amine (I) is discharged from the process. Formic acid and tertiary amine (I) are taken off via stream (4). This additionally comprises residual amounts of water.

Stream (4) is fed to the distillation apparatus C. In this, the formic acid is removed by distillation via stream (5) as overhead product, via stream (5a) as side product and/or via stream (5b) as side product. Depending on the boundary conditions, i.e. especially the composition of the feed stream (4) to the distillation apparatus C and the desired purity of the formic acid, formic acid can be obtained as stream (5) at the top or as stream (5a) as side product in the present embodiment. Water-comprising formic acid is then taken off as side product via stream (5a) or (5b). In some cases, it may even be sufficient to remove formic acid or water-comprising formic acid purely via stream (5) as overhead product. Depending on the specific embodiment, the side stream (5b) or even both side streams (5a) and (5b) can thus be dispensed with.

The bottom product from the distillation apparatus C is fed as stream (6) to the phase separation vessel D. As an alternative, the phase separator vessel D can also be integrated into the distillation apparatus C. The bottom product is separated into two liquid phases in the phase separation vessel D. A heat exchanger, for example, can also optionally be installed between the distillation apparatus C and the phase separation vessel D in order to cool the bottom stream taken off. Although a lower phase separation temperature generally leads to somewhat better separation in respect of the formic acid content, it results in an additional outlay and energy consumption because of the use of a heat exchanger. Advantages and disadvantages therefore have to be weighed against one another in each case.

The lower liquid phase from the phase separation vessel D is taken off as stream (7a) and recirculated as stream (7b) to the distillation apparatus C. In a preferred embodiment, part of stream (7a) can be taken off and fed as stream (7c) to the distillation apparatus G. In addition or as an alternative, the distillation apparatus G can also be supplied with other streams not shown here. Thus, for example, it is conceivable to introduce a substream of the bottom output from the distillation apparatus C into the distillation apparatus G. There, the stream is distilled under reduced pressure and part of the quaternary methylammonium formates is redissociated into tertiary amine (I), with the stream comprising formic acid and tertiary amine (I) being taken off at the top and fed as stream (7d) to the distillation apparatus B. The bottom product is discharged from the process.

The operating conditions of the distillation apparatus G, e.g. pressure, temperature, residence time, amount of feed stream, are generally a compromise between good dissociation conditions for the quaternary methylammonium formate at a very low degree of decomposition of formic acid. If the distillation apparatus G is not operated, quaternary methylammonium formates accumulate in the process, especially in the bottoms from the distillation apparatus C and in the lower phase from the phase separation vessel D, with the associated and above-described negative consequences for the process.

The upper liquid phase from the phase separation vessel D is taken off via stream (8a) and recirculated to the metering apparatus Y. The metering apparatus Y can be, for example, a reservoir provided with a fill level measurement and two regulated metering pumps for dispensing the streams (8d) and (8e). Furthermore, the metering apparatus Y can also comprise heating or cooling elements for controlling the temperature of the streams (8d) and (8e). A substream (8b) is fed to the distillation apparatus F. In this, low boilers are removed by distillation as stream (8z) and the stream depleted in low boilers is recirculated as stream (8c) to the metering apparatus Y.

In another, preferred embodiment for obtaining formic acid by hydrolysis of methyl formate, the methyl formate stream (1a) is introduced not directly into stage A1-i but into the distillation apparatus B. This embodiment is generally advantageous when the methyl formate available as stream (1a) is still contaminated with residual amounts of methanol, for example due to a preceding methyl formate synthesis stage with partial conversion of methanol and incomplete work-up of the methyl formate. As a result of the direct introduction of stream (1a) into the distillation apparatus B, the methanol comprised can be separated off as stream (3a) and, for example, recirculated to the methyl formate synthesis stage. This variant makes it possible to omit a methyl formate/methanol separation entirely in the methyl formate synthesis stage and thus to save an entire distillation column and thus also energy in ongoing operation.

In a further, preferred embodiment for obtaining formic acid by hydrolysis of methyl formate, both the methyl formate stream (1a) and the water stream (1b) are each introduced not directly into stage A1-i but into the distillation apparatus B. As regards the water stream (1b), this embodiment is generally advantageous when hot condensate or steam is available as water source, since in this way the thermal energy stored therein can be utilized in the distillation apparatus B.

For the sake of completeness, it may be mentioned that, in a further embodiment, it is naturally also possible to introduce the methyl formate stream (1a) into the apparatus A1-i but the water stream (1b) into the distillation apparatus B. This is advantageous when, for example, low-pressure excess steam is available.

In the variants mentioned, specific variants in respect of the embodiment of the distillation apparatus B having one, two or even three distillation columns are possible as disclosed, for example, in FIG. 12 to 13 of WO 2012/000,964. The variants having one or two distillation columns are preferred for the design of the distillation apparatus B. For the sake of completeness, it may be mentioned that, particularly in the embodiments having one or two distillation columns, these can also be configured as thermally coupled columns or a dividing wall column.

The process of the invention makes it possible to obtain formic acid starting from methyl formate in high yield and high concentration by thermal separation of a stream comprising formic acid and a tertiary amine.

The formation of undesirable organic degradation products of the tertiary amine (I) can be effectively reduced by the gradation according to the invention of the combining of methyl formate, water and tertiary amine (I). This enables, even without targeted removal and discharge of the degradation products mentioned, the concentration of these in the system to be kept at a low level over a prolonged period of time and negative effects to be significantly reduced. In addition, significantly less tertiary amine is irreversibly decomposed as a result of the measures according to the invention, so that significantly less fresh amine has to be introduced from the outside. This makes the process not only simpler but also relieves pressure on the environment by lower consumption.

Especially in combination with additional measures for removing and discharging the small amount of organic degradation products of the tertiary amine (I) which are still formed, for example the measures described in EP application No. 11 194 619.0 and EP application No. 11 194 607.5, gradual accumulation of low boilers can be particularly effectively countered. Disadvantages such as slow increase in the energy consumption in the distillation apparatus for thermal separation of the stream comprising formic acid and tertiary amine and also a slow deterioration in the quality of the formic as a result of increasing contamination with low boilers can thus be avoided particularly efficiently. The apparatuses for removing and discharging the abovementioned degradation products can also be made much smaller as a result of the measures according to the invention, which gives further advantages in the construction of the process apparatus and in ongoing operation.

The process of the invention can be operated very stably with, at the same time, constant high purity of the formic acid produced over long operating times. The formic acid obtained has a low color number and a high color number stability. The process can be carried out simply, reliably and with a low energy consumption.

Laboratory Plant 1

Figure 5:
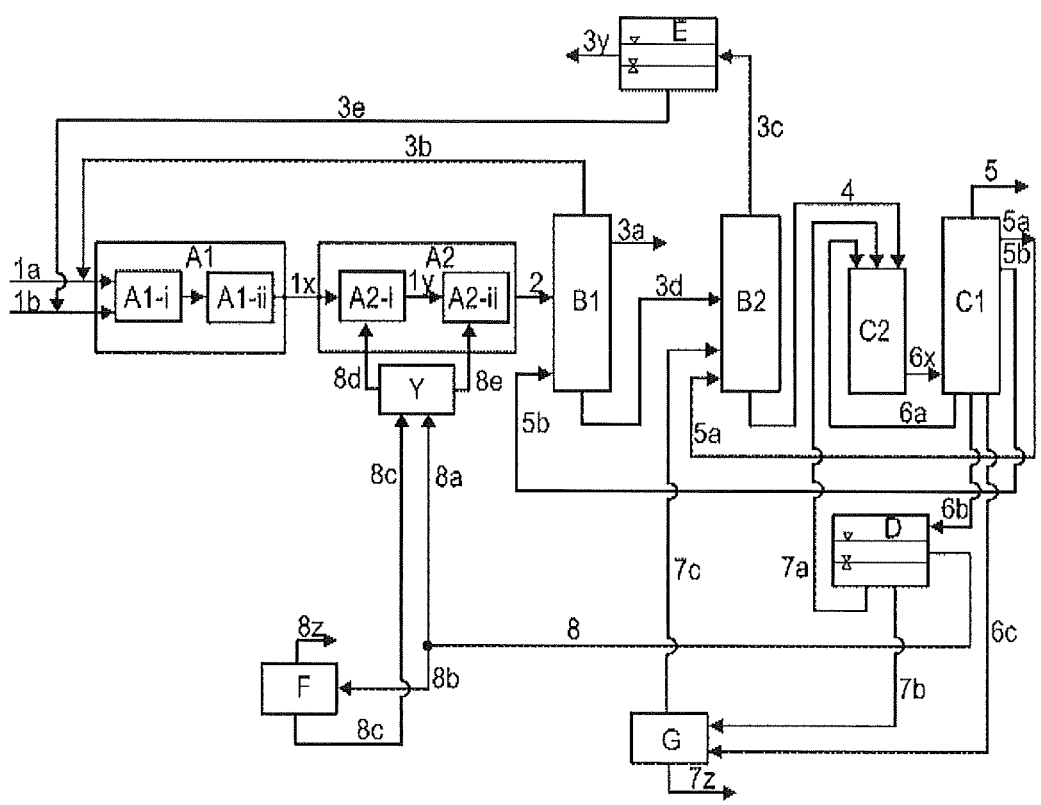
FIG. 5 shows a simplified block diagram of laboratory plant 1.

Laboratory plant 1 was employed for examining the continuous process. The simplified block diagram of laboratory plant 1 is shown in FIG. 5. In the figure, the individual letters have the following meaning:

A1=first stage of the apparatus for producing a stream comprising formic acid, tertiary amine (I) and water, which comprises the substages A1-i and A1-ii A1-i=stirred vessel (volume 0.3 l, electrically heated)

A1-ii=pipe reactor (internal diameter 80 mm, length 1200 mm, filled with 2 mm glass spheres, electrically heated)

A2=second stage of the apparatus for producing a stream comprising formic acid, tertiary amine (I) and water, which comprises the substages A2-i and A2-ii A2-i=tube reactor (internal diameter 80 mm, length 1200 mm, filled with 2 mm glass spheres, electrically heated)

A2-ii=tube reactor (internal diameter 80 mm, length 1200 mm, filled with 2 mm glass spheres, electrically heated)

Y=Vessel as a metering reservoir (5 l volume)

B1=Distillation apparatus comprising column body (internal diameter 55 mm, equipped with two mesh packings each having a packing height of 1.3 m and a specific surface area of 750 $m^2/m^3$, with the inlet for stream (2) being located between the two mesh packings), oil-heated falling film evaporator and condenser and also regulable runback distributor at the top of the column B2=Distillation apparatus comprising column body (internal diameter 55 mm, equipped with 12 bubble cap trays in the stripping section and 10 bubble cap trays in the enrichment section, with the inlet for stream (3d) being located between the two sections and the inlet for stream (5b) being located in the stripping section), oil-heated falling film evaporator and condenser and also regulable runback distributor at the top of the column C1=column body (internal diameter 43 mm, equipped with a mesh packing above the bottom having a packing height of 0.66 m and a specific surface area of 500 $m^2/m^3$ and also a further mesh packing having a packing height of 0.91 m and a specific surface area of 750 $m^2/m^3$, with the side offtake for stream (5b) being located between the two lower mesh packings and side offtake for stream (5a) being located between the two upper mesh packings) and condenser and also regulable runback distributor at the top of the column C2=oil-heated falling film evaporator D=separate phase separation vessel (volume 0.3 l, oil-heated)

E=phase separation vessel

F=distillation apparatus having a column body (internal diameter 30 mm, equipped with 1 m of Sulzer CY packing (750 $m^2/m^3$), with the inlet for stream (9a) being located beneath the packing), oil-heated bottom vessel and also regulable runback divider at the top of the column G=evaporation apparatus for removing high boilers and redissociating quaternary methylammonium formates (glass vessel having a volume of 2 l and oil-operated heating coil)

The apparatus and lines are composed of a nickel-based alloy having the material number 2.4610. The mass flows were measured by means of a coriolis flow meter. Laboratory plant 1 was operated continuously.

In all experiments in the laboratory plant 1, the content of formic acid was in each case determined by potentiometric titration with 0.5 N NaOH in water and the content of water was determined by the Karl Fischer method. All other organic components were in each case determined by gas chromatography.

Laboratory Plant 2

Laboratory plant 2 was employed for examining the decomposition of formic acid in the presence of methyltri-n-hexylammonium formate. It comprised a heated double-walled glass vessel K having an internal volume of 1 l for evaporation and a further, cooled vessel L having an internal volume of 1 l for condensation of the vaporized medium. An oil-heated heating coil was located in the lower part of the inner vessel of the double-walled glass vessel K. In addition, the double wall was also oil-heated. To regulate the flow into the double-walled glass vessel K, the latter comprised a fill level regulator. Between K and L, there was a condenser in which the vapor from K was condensed and introduced as such into L. The vessel L comprised both an outlet for condensed liquid product and for gaseous components. The level in the vessel L was always high enough for the condensed vapor from K to be introduced under the surface of the liquid. A flow meter was located in the outlet for gaseous components.

Determination of the Content of Methyltri-n-Hexylammonium Formate

The determination of the content of methyltri-n-hexylammonium formate was carried out by means of ion chromatography. To be able to analyze even low concentrations, each determination was carried out using a sample of about 1 l. Firstly, the low boilers (in particular methyl formate, methanol and water) were evaporated under reduced pressure at 3 hPa abs (3 mbar abs) and 30° C. The sample, which comprised formic acid, trihexylamine, methyltri-n-hexylammonium formate and possibly further intermediate and high boilers, was subsequently neutralized by means of 50% NaOH in water. This formed three phases: a heavy phase comprising an aqueous sodium formate solution, a middle phase comprising methyltri-n-hexylammonium formate and an upper, nonpolar amine phase. The phases were separated from one another and the content of methyltri-n-hexylammonium formate was determined in the middle phase by means of ion chromatography.

Determination of the Contents of Methyltripentylammonium Formate and Methyltri-n-Octylammonium Formate Apart from the determination by means of ion chromatography, the dissociation products of methyltri-n-hexylammonium formate were also determined by means of gas chromatography. Here, methyldihexylamine, which is not detectable in fresh tri-n-hexylamine, was found as characteristic dissociation product. Together with the result of the ion chromatography, the methyltri-n-hexylammonium formate could thus also be analyzed gas-chromatographically via its degradation products. This calibration was used for determining methyltripentylammonium formate and methyltri-n-octylammonium formate. Here, a sample of about 1 l of reaction output was used in each case. The low boilers (in particular methyl formate, methanol and water) were firstly evaporated at 30° C. under a reduced pressure of 3 hPa abs (3 mbar abs). The sample, which comprised formic acid, trialkylamine, methyltrialkylammonium formate and possibly further intermediate boilers and high boilers, was subsequently neutralized with 50% NaOH in water. This resulted in formation of three phases: a heavy phase comprising an aqueous sodium formate solution, a middle phase comprising methyltrialkylammonium formate and an upper, nonpolar amine phase. The phases were separated from one another and the content of methyltrialkylammonium formate in the middle phase was determined by means of the above-described gas-chromatographic method.

EXAMPLE 1

(Example According to the Invention in Laboratory Plant 1)

Example 1 was carried out in laboratory plant 1.2280 g/h of methyl formate via stream (1a) and 950 g/h of water via stream (1b) were metered by means of metering pumps into the strirred vessel A1-i. Methyl formate and water were in each case taken from a reservoir (not shown in FIG. 5 in the interests of simplicity) which had a volume of 5 l in each case and into which fresh methyl formate and water recirculated via streams (3b) and (3e) were introduced. The stirred vessel A1-i was operated at 110° C. and 1.3 MPa abs. The output from A1-i was introduced into the tube reactor A1-ii which was likewise operated at 110° C. and 1.3 MPa abs. The ratio n(amine to a1)/n(mefo to a1) was thus 0. The average residence time was 5 minutes in A1-i, and 36 minutes in the tube reactor A1-ii. A conversion of 87% of the hydrolysis equilibrium under the conditions set was achieved at the outlet of A1-ii. The output from A1-ii was then introduced via stream (1x) into the tube reactor A2-i. 1949 g/h of tri-n-hexylamine were introduced into this via stream (8d) from the reservoir Y having a volume of 5 l. The temperature in A2-i was 105° C. and the pressure was 1.3 MPa abs. The average residence time in A2-i was 22 minutes. 92% of the equilibrium conversion was achieved in the reaction output from A2-i. The output from A2-i was introduced into the tube reactor A2-ii into which a further 1947 g/h of tri-n-hexylamine were introduced via stream (8e) from the container Y. The tube reactor A2-ii was likewise operated at 105° C. and 1.3 MPa abs. The ratio n(amine to a2)/n(mefo to a1) was thus 0.38 and the ratio n(amine to a)/n(mefo to a) was likewise 0.38. A product mixture comprising 49.2% by weight of tri-n-hexylamine, 16.7% by weight of formic acid, 11.8% by weight of methanol, 7.2% by weight of water and 11.1% by weight of methyl formate was obtained as stream (2).

Stream (2) was depressurized and introduced into the column body of the distillation apparatus B1. In addition, 88 g/h of the water-rich side offtake stream from the column body of the distillation apparatus C1, comprising 82.7% by weight of formic acid and 17.3% by weight of water, was fed via stream (5b) to the distillation apparatus B1. At a pressure at the top of 0.18 MPa abs and a reflux ratio of 1.95, methyl formate was taken off as overhead product and methanol was taken off as side product. The methyl formate was recirculated as stream (3b) to the stirred vessel A1-i. As bottom product, 5790 g/h of a mixture comprising 71.2% by weight of tri-n-hexylamine, 9.1% by weight of water, 20.7% by weight of formic acid and 0.1% by weight of methanol was obtained as stream (3d). The temperature at the bottom of B1 was 119° C.

Stream (3d) was introduced into the column body of the distillation apparatus B2. In addition, 43 g/h of the relatively low-water side offtake stream from the column body of the distillation apparatus C1, which comprised 83.2% by weight of formic acid and 17.1% by weight of water, was fed via stream (5a) to the distillation apparatus B2. In addition, the condensed vapor stream from the evaporation apparatus G was also fed via stream (7c) to the distillation apparatus B2. At a temperature at the bottom of 177° C., a pressure at the top of 0.18 MPa abs and a reflux ratio of 0.26, stream (3c) was taken off as overhead product from B2 in an amount of 594 g/h and with a water content of 98.1% by weight and fed to the phase separation vessel E which was operated at 100° C. Stream (3e) was taken therefrom at the bottom and recirculated via a reservoir to the stirred vessel A1-i. Some days after start-up of the plant, a further, upper phase which comprised the organic degradation products of tri-n-hexylamine which had been separated off together with the water slowly formed. This upper phase was then removed daily as stream (3y).

As bottom product, 5496 g/h of a mixture comprising 66.8% by weight of tri-n-hexylamine, 24.7% by weight of formic acid and 1.1% by weight of water were obtained from the distillation apparatus B2. This was fed as stream (4) from the top into the evaporator C2. In addition, stream (6a) from the bottom of the column body C1 and stream (7a) from the lower liquid phase from the phase separation vessel D were also fed to the evaporator C2. The evaporator C2 and the column body C1 were operated at reduced pressure. The temperature at the lower outlet of the evaporator C2 was 156° C. The output from the evaporator was fed as stream (6x) to the column body C1. This was operated at a pressure at the top of 150 hPa abs and a reflux ratio of runback to distillate of 3. As overhead product from C1, 987 g/h of 99.6% strength by weight of formic acid were obtained as stream (5). The content of n-hexyl formate in stream (5) was <10 ppm by weight, and the content of n-hexanal was <15 ppm by weight. The side offtake stream (5a) was recirculated to the distillation apparatus B2 and the side offtake stream (5b) was recirculated to the distillation apparatus B1. Stream (6b) was taken off in an amount of 5024 g/h from the bottom of the column body C1 and introduced into the phase separation vessel D. Furthermore, a stream of 147 g/h was taken off from the bottom of the column body C1 and fed as stream (6c) to the evaporation apparatus G.

The phase separation vessel D was operated at atmospheric pressure and a temperature of 80° C. Two liquid phases were formed. The upper liquid phase was continuously taken off as stream (8) in an amount of 3945 g/h and conveyed via stream (8a) into the container Y. Stream (8) comprised 94.1% by weight of tri-n-hexylamine and 1.9% by weight of formic acid. The lower liquid phase was taken off continuously as stream (7a) and conveyed to the evaporator C2. In parallel thereto, a stream of 80 g/h was taken off as stream (7b) from the lower liquid phase and fed to the evaporation apparatus G.

The evaporation apparatus G was operated at a pressure of 20 hPa abs and a temperature of 165° C. The vapor was condensed and introduced as stream (7c) into the distillation apparatus B2. After an operating time of 2 months, the evaporation G was cooled, depressurized and emptied. An amount of about 1100 g was taken off as stream (7z) from the bottoms and discharged. Stream (7z) comprised high boilers such as relatively high molecular weight secondary components and also traces of metals from the apparatus.

33 g/h were taken off from stream (8) via stream (8b) and fed to the distillation apparatus F. At a pressure of 15 hPa abs and a temperature at the bottom of 162° C., 0.5 g/h of distillate were taken off as stream (8z) and discarded. The remainder was fed as stream (8c) to the container Y.

To ensure a stable operating state, the plant was firstly run-in for 14 days and a sample was then taken from the output from the tube reactor A2-i (stream (1y)) and analyzed to determine the content of methyltri-n-hexylammonium formate. The concentration of methyltri-n-hexylammonium formate in this stream was 83 ppm by weight.

EXAMPLE 2

(Example According to the Invention in Laboratory Plant 1)
Example 2 was carried out in a manner analogous to example 1 except for the modifications indicated below:
Stirred vessel A1-i and tube reactor A1-ii were operated at 130° C.
The hydrolysis equilibrium in the output from A1-ii was 88%.
Stream (8d) was 1944 g/h.
Tube reactor A2-i was operated at 128° C.
The hydrolysis equilibrium in the output from A2-i was 93%.
Stream (8e) was 1945 g/h.
Tube reactor A2-ii was operated at 131° C.
The ratio n(amine to a1)/n(mefo to a1) was thus likewise 0, and the ratio n(amine to a2)/n(mefo to a1) was likewise 0.38. The ratio n(amine to a)/n(mefo to a) was also the same at 0.38.
To ensure a stable operating state, the plant was firstly run-in under the conditions of example 2 until a 5-fold exchange in all plant parts was ensured and a sample was then taken from the output from the tube reactor A2-i (stream (1y)) and analyzed to determine the content of methyltri-n-hexylammonium formate. The concentration of methyltri-n-hexylammonium formate in this stream was 508 ppm by weight.
The plant was operated in a stable fashion over a period of a number of months.
Examples 1 and 2 show that the process of the invention can be operated in a stable fashion over a prolonged period of time. The contents of methyltri-n-hexylammonium formate were, at 83 ppm by weight (=0.0083% by weight) in example 1 and 508 ppm by weight (=0.0508% by weight) in example 2, in a relatively small range. However, the two examples also show that the formation of methyltri-n-hexylammonium formate increases significantly with increasing hydrolysis temperature in step (a2). Increasing the temperature from 105° C. in example 1 to about 130° C. in example 2 led to an increase in the content of methyltri-n-hexylammonium formate by a factor of about six.

EXAMPLES 3 TO 5

(Formation of Methyltri-n-Hexylammonium Formate in Laboratory Plant 1)
Only the apparatuses A1 (comprising A1-i and A1-ii), A2 (comprising A2-i and A2-ii) and Y of the laboratory plant 1 were operated for examples 3 to 5. Fresh methyl formate and fresh water were introduced via the streams (1a) and (1b), respectively, and fresh tri-n-hexylamine from vessel Y was introduced via the streams (8d) and (8e). Stream (1y) was analyzed to determine its content of methyltri-n-hexylammonium formate. The process conditions and the results are shown in table 1.
Examples 3 to 5 show that, under otherwise analogous conditions, splitting of the addition of tri-n-hexylamine in step (a2) leads to a reduction in the formation of methyltri-n-hexylammonium formate. Thus, stream (1y) in example 3 without split addition comprised 770 ppm by weight of methyltri-n-hexylammonium formate, but stream (1y) in example 4 with a 50%/50% split comprised only 508 ppm by weight. In addition, the examples show a significant reduction in the formation of methyltri-n-hexylammonium formate when the hydrolysis temperature is reduced under otherwise analogous conditions. Thus, stream (1y) in example 4 at a hydrolysis temperature of about 130° C. comprised 508 ppm by weight of methyltri-n-hexylammonium formate, but stream (1y) in example 4 at a hydrolysis temperature of about 105° C. comprised only 83 ppm by weight.

EXAMPLES 6 TO 8

(Decomposition of Formic Acid in the Presence of Methyl-tri-n-Hexylammonium Formate)
Examples 6 to 8 were carried out in laboratory plant 2. Here, a stream comprising formic acid, tri-n-hexylamine (THA), methyldi-n-hexylamine (MDHA), methyltri-n-hexylammonium formate (MTHA formate), di-n-hexylformamide (DHF) and water were fed in a regulated amount into the heated double-walled glass vessel K in such a way that about 1 l was present therein in each case. The vaporized components was condensed and collected at about 20° C. in vessel L. The amount of gaseous output from the vessel L was determined by means of a flow meter. The gaseous output was additionally analyzed by gas chromatography to determine the volumes of hydrogen, carbon dioxide and carbon monoxide. The process conditions and the results are shown in table 2.
Examples 6 to 8 demonstrate that, under otherwise comparable conditions, the decomposition of formic acid increases significantly with the concentration of methyltri-n-hexylammonium formate. Thus, for example, 7.4% of the introduced formic acid decomposes at a content of MTHA formate of 0.08% by weight in example 7, while the value at a content of MTHA formate of 0.68% by weight in example 8 is 13.5% and at a content of MTHA formate of 1.7% by weight in example 6 is as high as 23.9%. The contents of tri-n-hexylamine (THA) and the other organic degradation products of THA, e.g. MDHA and DHF, were at a very similar level (variation about ±12% relative) in the examples.
Examples 6 to 8 therefore very impressively show that MTHA formate as representative of quaternary methylammonium formates very strongly promotes the undesirable decomposition of formic acid and its concentration should therefore ideally be kept very low in the process for obtaining formic acid. Precisely this is brought about by the measures according to the invention.

EXAMPLES 9-10

(Redissociation of Methyltri-n-Hexylammonium Formate)

EXAMPLE 9

118.0 g of a mixture comprising 12.6 g of formic acid and 105.4 g of tri-n-hexylamine (THA) were introduced into a 1 l double-walled glass vessel. No methyldi-n-hexylamine (MDHA) could be detected in this mixture. The reaction solution was heated to 163° C. A pressure of 250 mbara was applied by means of a vacuum pump. The discharge of low-boiling secondary components such as methyl formate was made possible by means of a rocking funnel without losing higher-boiling components such as MDHA. 12.5 g of a solution comprising 7.6 g of methyltri-n-hexylammonium formate, 2.0 g of formic acid and 2.9 g of tri-n-hexylamine was introduced. The mixture was maintained at the previously set temperature for 6.1 hours. 99.5 g of a two-phase mixture were obtained as output. To be able to determine the ammonium formate content by analysis, 50.5 g of formic acid were added to effect homogenization after cooling, giving a total mass of the output of 150.1 g. A residual content of 3.71% by weight of methyltri-n-hexylammonium formate was found in this solution by means of ion chromatography. Thus, 5.6 g of methyltri-n-hexylammonium formate were still present after the reaction, indicating that 2.0 g of methyltri-n-hexylammonium formate were decomposed during the reaction (=26.3%). Furthermore, 0.6 g of MDHA were detected in the reaction output by means of gas chromatography. This amount corresponds in molar terms to 1.0 g of methyltri-n-hexylammonium formate.

EXAMPLE 10

122.2 g of a mixture comprising 12.2 g of formic acid and 110.0 g of tri-n-hexylamine (THA) were introduced into a 1 l double-walled glass vessel. The reaction solution was heated to 173° C. A pressure of 300 mbara was applied by means of a vacuum pump. The discharge of low-boiling secondary components such as methyl formate was made possible by means of a rocking funnel without losing higher-boiling components such as methyldi-n-hexylamine (MDHA). 11.6 g of a solution comprising 7.0 g of methyltri-n-hexylammonium formate, 1.9 g of formic acid and 2.7 g of tri-n-hexylamine were introduced. The mixture was maintained at the previously set temperature for 6.1 hours. 121.3 g of a two-phase mixture were obtained as output. To be able to determine the methyltri-n-hexylammonium formate content by analysis, 34.5 g of formic acid were added to effect homogenization after cooling, giving a total mass of the output of 155.8 g. A residual content of 2.32% by weight of methyltri-n-hexylammonium formate was found in this solution by means of ion chromatography. Thus, 3.6 g of methyltri-n-hexylammonium formate were still present after the reaction, indicating that 3.4 g of methyltri-n-hexylammonium formate were decomposed during the reaction (=48.6%). Furthermore, 1.1 g of MDHA were detected in the reaction output by means of gas chromatography. Accordingly, 1.7 g of methyltri-n-hexylammonium formate (50%) were decomposed into MDHA.

Examples 9 and 10 clearly show that methyltri-n-hexylammonium formate is dissociated at elevated temperatures and 50% of the dissociated methyltri-n-hexylammonium formate is dissociated into MDHA.

EXAMPLES 11-13

(Influence of the Splitting of the Amine Addition on the Formation of Methyltri-n-Hexylammonium Formate from Tri-n-Hexylamine)

EXAMPLE 11

600 g of methyl formate, 252 g of water and 1076 g of tri-n-hexylamine were introduced into an autoclave and maintained at 130° C. and 25 bar abs for 2 hours. The autoclave was subsequently cooled to room temperature and depressurized. Analysis of the output from the autoclave indicated a mixture comprising 17.5% by weight of formic acid, 6.5% by weight of water and 14.1% by weight of methanol and also 0.16% by weight of methyltri-n-hexylammonium formate. The experimental conditions and selected analytical values are shown in Tables 3a and 3b.

EXAMPLE 12

600 g of methyl formate and 252 g of water were introduced into an autoclave and maintained at 130° C. at 25 bar abs for 1 hour. 1076 g of tri-n-hexylamine were subsequently injected and the mixture was again maintained at 130° C. and 25 bar abs for 1 hour. The autoclave was then cooled to room temperature and depressurized. Analysis of the output from the autoclave indicated a mixture comprising 16.3% by weight of formic acid, 6.5% by weight of water and 13.6% by weight of methanol and also 0.11% by weight of methyltri-n-hexylammonium formate. The experimental conditions and selected analytical values are shown in Tables 3a and 3b.

Compared to Example 11, significantly less methyltri-n-hexylammonium formate (0.11% by weight compared to 0.16% by weight in Example 11) was formed as a result of the stepwise additions according to the invention of methyl formate and of water in stage (a1) and of the tertiary amine in stage (a2) under otherwise identical conditions and with the same (within analytical accuracy) amount of formic acid being formed. This corresponds to a reduction by 31% relative.

EXAMPLE 13

600 g of methyl formate and 252 g of water were introduced into an autoclave and maintained at 130° C. at 25 bar abs for 1 hour. 538 g of tri-n-hexylamine were subsequently injected and the mixture was maintained at 130° C. at 25 bar abs for 0.5 hour. A further 538 g of tri-n-hexylamine were then introduced in this way and the mixture was maintained at 130° C. at 25 bar abs for a further 0.5 hour. The autoclave was then cooled to room temperature and depressurized. Analysis of the output from the autoclave indicated a mixture comprising 16.7% by weight of formic acid, 6.6% by weight of water and 13.6% by weight of methanol and also 0.08% by weight of methyltri-n-hexylammonium formate. The experimental conditions and selected analytical values are shown in Tables 3a and 3b.

The preferred, compared to Example 12, division of the addition of the tertiary amine in stage (a2) with addition of one part in substage (a2-i) and a further part in substage (a2-ii) enabled the formation of methyltri-n-hexylammonium formate to be significantly reduced further (0.08% by weight compared to 0.11% by weight in Example 12) under otherwise identical conditions and with the same amount, within analytical accuracy, of formic acid being formed. Compared to Example 11, this corresponds to a reduction by 50% relative.

EXAMPLE 14

600 g of methyl formate, 252 g of water and 269 g of tri-n-hexylamine were introduced into an autoclave and maintained at 130° C. at 25 bar abs for 1 hour. 403 g of tri-n-hexylamine were subsequently injected and the mixture was maintained at 130° C. at 25 bar abs for 0.5 hour. A further 403 g of tri-n-hexylamine were then introduced in this way and the mixture was maintained at 130° C. at 25 bar abs for a further 0.5 hour. The autoclave was then cooled to room temperature and depressurized. Analysis of the output from the autoclave indicated a mixture comprising 16.4% by weight of formic acid, 6.4% by weight of water and 12.7% by weight of methanol and also 0.10% by weight of methyltri-n-hexyl formate. The experimental conditions and selected analytical values are shown in Tables 4a and 4b.

Example 14 shows that even when a small amount of the tertiary amine is introduced into stage (a1) in a molar ratio of n(amine to a1)/n(mefo to a1) of 0.1 and subsequent splitting of the further introduction of amine into substages (a2-i) and (a2-ii), a significant reduction in the formation of methyltri-n-hexylammonium formate (MTHA formate) is achieved in comparison with introduction of all of the tertiary amine into stage (a1), as in comparative Example 11. Thus, only 0.10% by weight of MTHA formate were formed in Example 14, while 0.16% by weight were formed in Example 11. The value of 0.10% by weight of MTHA formate achieved in Example 14 is even minimally lower than that in Example 12 and only slightly higher than that in Example 13. The amount of formic acid formed was the same within analytical accuracy.

EXAMPLE 15

(Influence of the Temperature in the Case of Split Amine Addition on the Formation of Methyltri-n-Hexylammonium Formate from Tri-n-Hexylamine)

Example 15 was carried out like Example 13 but a temperature of only 105° C. was set in substages (a2-i) and (a2-ii). Analysis of the reaction output indicated a mixture comprising 17.2% by weight of formic acid, 6.5% by weight of water and 13.0% by weight of methanol and also 0.02% by weight of methyltri-n-hexylammonium formate.

Lowering the temperature in substages (a2-i) and (a2-ii) from 130° C. to 105° C. under otherwise identical conditions and with the same, within analytical accuracy, amount of formic acid being formed enabled a further, significant reduction in the formation of methyltri-n-hexylammonium formate (MTHA formate) from 0.08% by weight in Example 13 to 0.02% by weight in Example 15 to be achieved.

EXAMPLES 16-17

(Influence of the Splitting of the Amine Addition on the Formation of MethyltripentylAmmonium Formate from Tripentylamine)

EXAMPLE 16

600 g of methyl formate, 252 g of water and 910 g of tripentylamine were introduced into an autoclave and maintained at 130° C. and 25 bar abs for 2 hours. The autoclave was then cooled to room temperature and depressurized. Analysis of the output from the autoclave indicated a mixture comprising 18.2% by weight of formic acid, 7.6% by weight of water and 13.5% by weight of methanol and also 0.05% by weight of methyltripentylammonium formate. The experimental conditions and selected analytical values are shown in Table 5.

EXAMPLE 17

600 g of methyl formate and 252 g of water were introduced into an autoclave and maintained at 130° C. and 25 bar abs for 1 hour. 910 g of tripentylamine were subsequently injected and the mixture was again maintained at 130° C. at 25 bar abs for 1 hour. The autoclave was then cooled to room temperature and depressurized. Analysis of the output from the autoclave indicated a mixture comprising 17.8% by weight of formic acid, 7.4% by weight of water, 13.7% by weight of methanol and also 0.02% by weight of methyltripentylammonium formate. The experimental conditions and selected analytical values are shown in Table 5.

Compared to Example 16, significantly less methyltripentylammonium formate (0.02% by weight compared to 0.05% by weight in Example 16) was formed as a result of the stepwise additions according to the invention of methyl formate and of water in stage (a1) and of the tertiary amine in stage (a2) under otherwise identical conditions and with the same (within analytical accuracy) amount of formic acid being formed. This corresponds to a reduction by 60% relative.

EXAMPLES 18-19

(Influence of the Splitting of the Amine Addition on the Formation of Methyltri-n-Octylammonium Formate from Tri-n-Octylamine)

EXAMPLE 18

540 g of methyl formate, 227 g of water and 1273 g of tri-n-octylamine were introduced into an autoclave and maintained at 130° C. and 25 bar abs for 2 hours. The autoclave was then cooled to room temperature and depressurized. Analysis of the output from the autoclave indicated a mixture comprising 14.3% by weight of formic acid, 4.4% by weight of water and 10.4% by weight of methanol and also 0.23% by weight of methyltri-n-octylammonium formate. The experimental conditions and selected analytical values are shown in Table 6.

EXAMPLE 19

In Example 19, 339 g of methyl formate, 167 g of water, 154 g of formic acid and 107 g of methanol were introduced into an autoclave and together with 1273 g of tri-n-octylamine maintained at 130° C. at 25 bar for 1 hour. The autoclave was then cooled to room temperature and depressurized. Analysis of the output from the autoclave indicated a mixture comprising 13.2% by weight of formic acid, 5.3% by weight of water and 13.0% by weight of methanol and also 0.17% by weight of methyltri-n-octylammonium formate.

The amounts of methyl formate, water, formic acid and methanol used correspond to those present in the hydrolysis of 540 g of methyl formate and 227 g of water after 1 hour at 130° C. at 25 bar abs. The use of the four components mentioned is thus equivalent to stage (a1). The reaction with tri-n-octylamine corresponds to stage (a2-i). The experimental conditions and selected analytical values are shown in Table 6.

Compared to Example 18, significantly less methyltri-n-hexylammonium formate (0.17% by weight compared to 0.23% by weight in Example 18) was formed as a result of the stepwise additions according to the invention of methyl formate and of water in stage (a1), which was modeled by addition of a corresponding mixture of methyl formate, water, formic acid and methanol, and of the tertiary amine in stage (a2) under otherwise identical conditions and with the same (within analytical accuracy) amount of formic acid being formed. This corresponds to a reduction by 26% relative.

TABLE 1

| Parameter | Example 3 | Example 4 | Example 5 |
|---|---|---|---|
| Stream (1a) (methyl formate) | 2280 g/h | 2280 g/h | 2280 g/h |
| Stream (1b) (water) | 950 g/h | 950 g/h | 950 g/h |
| Temperature in A1-i | 130° C. | 130° C. | 105° C. |
| Temperature in A1-ii | 130° C. | 130° C. | 105° C. |
| Stream (8d) tri-n-hexylamine | 3890 g/h | 1944 g/h | 1949 g/h |
| Temperature in A2-i | 133° C. | 128° C. | 105° C. |
| Stream (8e) tri-n-hexylamine | — | 1945 g/h | 1947 g/h |
| Temperature in A2-ii | 131° C. | 131° C. | 109° C. |
| n(amine to a1)/n(mefo to a1) | 0 | 0 | 0 |
| Hydrolysis equilibrium at the outlet from A1-ii | 92% | 92% | 90% |
| n(amine to a2)/n(mefo to a1) | 0.38 | 0.38 | 0.38 |
| Hydrolysis equilibrium at the outlet of A2-i | 93% | 96% | 95% |
| n(amine to a)/n(mefo to a) | 0.38 | 0.38 | 0.38 |
| n(amine to a2-i)/n(amine to a2-ii) (amine split in step a2) | 100%/0% | 50%/50% | 50%/50% |
| Content of methyltri-n-hexylammonium formate | 770 ppm by weight | 508 ppm by weight | 83 ppm by weight |

TABLE 2

| Parameter | Example 6 | Example 7 | Example 8 |
|---|---|---|---|
| Stream fed to vessel K | 137 g/h | 134 g/h | 121 g/h |
| Formic acid | 13.4% by weight | 10.7% by weight | 14.4% by weight |
| THA | 76.7% by weight | 80.0% by weight | 75.8% by weight |
| MDHA | 4.2% by weight | 4.4% by weight | 5.3% by weight |
| MTHA formate | 1.7% by weight | 0.08% by weight | 0.68% by weight |
| DHF | 3.7% by weight | 3.1% by weight | 3.5% by weight |
| Pressure in vessel K | 20 hPa abs | 15 hPa abs | 20 hPa abs |
| Temperature in vessel K | 170° C. | 165° C. | 170° C. |
| Gaseous output from vessel L | 5.1 standard l/h | 2.0 standard l/h | 3.2 standard l/h |
| Hydrogen | 37.7% by volume | 23.0% by volume | 28.8% by volume |
| Carbon dioxide | 36.2% by volume | 23.3% by volume | 28.5% by volume |
| Carbon monoxide | 4.9% by volume | 2.8% by volume | 9.9% by volume |
| Decomposition of the formic acid introduced | 23.9% | 7.4% | 13.5% |

THA: Tri-n-hexylamine
MDHA: Methyldi-n-hexylamine
MTHA formate: Methyltri-n-hexylammonium formate
DHF: Di-n-hexylformamide TABLE 3a

| Parameter | Example 11 | Example 12 | Example 13 |
|---|---|---|---|
| Stage (a1) | | | |
| Starting mixture | 600 g of mefo 252 g of H$_2$O 1076 g of THA | 600 g of mefo 252 g of H$_2$O | 600 g of mefo 252 g of H$_2$O |
| Time | 2 h | 1 h | 1 h |
| Temperature | 130° C. | 130° C. | 130° C. |
| Pressure | 25 bar abs | 25 bar abs | 25 bar abs |
| n(amine to a1)/n(mefo to a1) | 0.4 | 0 | 0 |
| Hydrolysis equilibrium attained | >96% | >96% | >96% |
| Stage (a2-i) | | | |
| Introduction into (a2-i) | | 1076 g of THA | 538 g of THA |
| Time | | 1 h | 0.5 h |
| Temperature | | 130° C. | 130° C. |
| Pressure | | 25 bar abs | 25 bar abs |
| n(amine to a2-i)/n(mefo to a1) | | 0.4 | 0.2 |
| Hydrolysis equilibrium attained | | >96% | >96% |

TABLE 3a-continued

| Parameter | Example 11 | Example 12 | Example 13 |
|---|---|---|---|
| Stage (a2-ii) | | | |
| Introduction into (a2-ii) | | | 538 g of THA |
| Time | | | 0.5 h |
| Temperature | | | 130° C. |
| Pressure | | | 25 bar abs |
| n(amine to a2-ii)/n(mefo to a1) | | | 0.2 |
| Hydrolysis equilibrium attained | | | >96% |

TABLE 3b

| Parameter | Example 11 | Example 12 | Example 13 |
|---|---|---|---|
| Results | | | |
| n(amine to a)/n(mefo to a) | 0.4 | 0.4 | 0.4 |
| Amine split in stage (a2) | — | 100%/0% | 50%/50% |
| n(amine to a2-i)/n(amine to a2-ii) | | | |
| Weight of end product | 1837 g | 1817.2 g | 1738.5 g |
| Amount of MTHA formate in end product | 2.96 g | 2.00 g | 1.49 g |
| Proportion of MTHA formate in end product | 0.16% by weight | 0.11% by weight | 0.08% by weight | mefo: methyl formate
THA: tri-n-hexylamine
MTHA formate: methyltri-n-hexylammonium formate

TABLE 4a

| Parameter | Example 14 | Example 15 |
|---|---|---|
| Stage (a1) | | |
| Starting mixture | 600 g of mefo<br>252 g of H$_2$O<br>269 g of THA | 600 g of mefo<br>252 g of H$_2$O |
| Time | 1 h | 1 h |
| Temperature | 130° C. | 130° C. |
| Pressure | 25 bar abs | 25 bar abs |
| n(amine to a1)/n(mefo to a1) | 0.1 | 0 |
| Hydrolysis equilibrium attained | >96% | >96% |
| Stage (a2-i) | | |
| Introduction into (a2-i) | 403 g of THA | 538 g of THA |
| Time | 0.5 h | 0.5 h |
| Temperature | 130° C. | 105° C. |
| Pressure | 25 bar abs | 25 bar abs |
| n(amine to a2-i)/n(mefo to a1) | 0.15 | 0.2 |
| Hydrolysis equilibrium attained | >96% | >96% |
| Stage (a2-ii) | | |
| Introduction into (a2-ii) | 403 g of THA | 538 g of THA |
| Time | 0.5 h | 0.5 h |
| Temperature | 130° C. | 105° C. |
| Pressure | 25 bar abs | 25 bar abs |
| n(amine to a2-ii)/n(mefo to a1) | 0.15 | 0.2 |
| Hydrolysis equilibrium attained | >96% | >96% |

TABLE 4b

| Parameter | Example 14 | Example 15 |
|---|---|---|
| Results | | |
| n(amine to a)/n(mefo to a) | 0.4 | 0.4 |
| Amine split in stage (a2) | 50%/50% | 50%/50% |
| n(amine to a2-i)/n(amine to a2-ii) | | |
| Weight of end product | 1857 g | 1779.6 g |
| Amount of MTHA formate in end product | 1.85 g | 0.35 g |
| Proportion of MTHA formate in end product | 0.10% by weight | 0.02% by weight | mefo: methyl formate
THA: tri-n-hexylamine
MTHA formate: methyltri-n-hexylammonium formate

TABLE 5

| Parameter | Example 16 | Example 17 |
|---|---|---|
| Stage (a1) | | |
| Starting mixture | 600 g of mefo<br>252 g of H$_2$O<br>910 g of TPA | 600 g of mefo<br>252 g of H$_2$O |
| Time | 2 h | 1 h |
| Temperature | 130° C. | 130° C. |
| Pressure | 25 bar abs | 25 bar abs |
| n(amine to a1)/n(mefo to a1) | 0.4 | 0 |
| Hydrolysis equilibrium attained | >96% | >96% |
| Stage (a2-i) | | |
| Introduction into (a2-i) | | 910 g of TPA |
| Time | | 1 h |
| Temperature | | 130° C. |
| Pressure | | 25 bar abs |
| n(amine to a2-i)/n(mefo to a1) | | 0.4 |
| Hydrolysis equilibrium attained | | >96% |
| Results | | |
| n(amine to a)/n(mefo to a) | 0.4 | 0.4 |
| Amine split in stage (a2) | — | — |
| n(amine to a2-i)/n(amine to a2-ii) | | |
| Weight of end product | 1656.9 g | 1642 g |
| Amount of MTPA formate in end product | 0.85 g | 0.33 g |
| Proportion of MTPA formate in end product | 0.05% by weight | 0.02% by weight | mefo: methyl formate
TPA: tripentylamine
MTPA formate: methyltripentylammonium formate

TABLE 6

| Parameter | Example 18 | Example 19 |
|---|---|---|
| Stage (a1) | | |
| Starting mixture | 540 g of mefo | 339 g of mefo |
| | 227 g of H$_2$O | 167 g of H$_2$O |
| | 1273 g of TOA | 154 g of FA |
| | | 107 g of MeOH |
| Time | 2 h | |
| Temperature | 130° C. | |
| Pressure | 25 bar abs | |
| n(amine to a1)/n(mefo to a1) | 0.4 | |
| Hydrolysis equilibrium attained | >96% | |
| Stage (a2-i) | | |
| Introduction into (a2-i) | | 1273 g of TOA |
| Time | | 1 h |
| Temperature | | 130° C. |
| Pressure | | 25 bar abs |
| n(amine to a2-i)/n(mefo to a1) | | 0.4 |
| Hydrolysis equilibrium attained | | ≈92% |
| Results | | |
| n(amine to a)/n(mefo to a) | 0.4 | 0.4 |
| Amine split in stage (a2) n(amine to a2-i)/n(amine to a2-ii) | — | — |
| Weight of end product | 1975 g | 1988 g |
| Amount of MTOA formate in end product | 4.45 g | 3.38 g |
| Proportion of MTOA formate in end product | 0.23% by weight | 0.17% by weight | mefo: methyl formate
TOA: tri-n-octylamine
MTOA formate: methyltri-n-octylammonium formate
FA: formic acid
MeOH: methanol

The invention claimed is:

1. A process for obtaining formic acid by thermal separation of a stream comprising formic acid and a tertiary amine (I) which at a pressure of 1013 hPa abs has a boiling point which is at least 5° C. higher than that of formic acid, in which
   (a) producing a liquid stream comprising formic acid, methanol, water and tertiary amine (I) by combining methyl formate, water and tertiary amine (I) at a temperature of from 50 to 200° C.;
   (b) separating from 10 to 100% by weight of the methanol produced from step (a); and
   (c) distilling formic acid from the liquid stream of step (b) comprising formic acid, water and tertiary amine (I) in a distillation apparatus at a bottom temperature of from 100 to 300° C. and a pressure of from 30 to 3000 hPa abs;
   wherein, when methyl formate, water and tertiary amine (I) are combined in step (a),
   (a1) methyl formate, water and optionally tertiary amine (I) are introduced in step (a1), where the molar ratio of the tertiary amine (I) optionally introduced into step (a1), n(amine to a1), to the methyl formate introduced into step (a1), n(mefo to a1), is $0 \leq n(\text{amine to a1})/n(\text{mefo to a1}) \leq 0.1$, and from 70 to 100% of the hydrolysis equilibrium possible under the prevailing conditions is set at a temperature of from 50 to 200° C. and,
   (a2) in step (a2), tertiary amine (I) is subsequently introduced into the stream obtained in step (a1), where the molar ratio of the tertiary amine (I) introduced in step (a2) into the stream obtained in step (a1), n(amine to a2), to the methyl formate introduced into step (a1), n(mefo to a1), is $0.1 \leq n(\text{amine to a2})/n(\text{mefo to a1}) \leq 2$, where the molar ratio of the total tertiary amine (I) introduced into step (a) "n(amine to a)" to the total methyl formate introduced into step (a) "n(mefo to a)" is at least 0.1.

2. The process according to claim 1, wherein a ratio of an available empty reactor volume for the reaction of step (a1) to an available empty volume for the reaction of step (a2) is from 0.1 to 10.

3. The process according to claim 1, wherein the molar ratio of n(amine to a1)/n(mefo to a1) in step (a1) is from 0 to 0.05.

4. The process according to claim 1, wherein the hydrolysis in step (a1) is carried out at a temperature of from 70 to 150° C.

5. The process according to claim 1, wherein the molar ratio of n(amine to a2)/n(mefo to a1) in step (a2) is ≤1.

6. The process according to claim 1, wherein the hydrolysis in step (a2) is carried out at a temperature of from 70 to 150° C.

7. The process according to claim 1, wherein the tertiary amine (I) is introduced in a gradated manner in step (a2).

8. The process according to claim 7, wherein the tertiary amine (I) is introduced in from 2 to 100 substeps in step (a2).

9. The process according to claim 8, wherein, in step (a2), not more than 90% of the total amount of the stream n(amine to a2) is introduced in a substep.

10. The process according to claim 9, wherein, in step (a2), from 20 to 80% of the total amount of the stream n(amine to a2) is introduced in one substep and from 20 to 80% of the total amount of the stream n(amine to a2) is introduced in a subsequent substep, and from 70 to 100% of the hydrolysis equilibrium possible under the prevailing conditions is set before the subsequent substep.

11. The process according to claim 1, wherein the tertiary amine (I) to be used in step (a) and the degree of separation in the distillation apparatus mentioned in step (c) are selected so that two liquid phases are formed in the bottom output from the distillation apparatus mentioned in step (c),
    (d) the bottom output from the distillation apparatus of step (c) is separated into two liquid phases, where the upper liquid phase has a molar ratio of formic acid to tertiary amine (I) of from 0 to 0.5 and the lower liquid phase has a molar ratio of formic acid to tertiary amine (I) of from 0.5 to 4;
    (e) the upper liquid phase from the phase separation in step (d) is recirculated to step (a); and
    (f) the lower liquid phase from the phase separation in step (d) is recirculated to step (b) and/or (c).

12. The process according to claim 11, wherein the degree of separation in the distillation apparatus mentioned in step (c) is selected so that the molar ratio of formic acid to tertiary amine (I) in the bottom output is from 0.1 to 2.0.

13. The process according to claim 11, wherein
    (g) formic acid and tertiary amine (I) are distilled off from the lower liquid phase from the phase separation in step (d) in a distillation apparatus at a temperature at the bottom of from 80 to 300° C. and a pressure of from 1 to 1000 hPa abs and the stream which has been distilled off is recirculated to one of the abovementioned steps (a) to (f).

14. The process according to claim 13, wherein from 0.01 to 50% of the lower liquid phase from the phase separation in step (d) is fed to step (g).

15. The process according to claim 1, wherein an amine of the general formula (Ia) is used as tertiary amine (I),

where the radicals $R^1$ to $R^3$ are identical or different and are each, independently of one another, an unbranched or branched, acyclic or cyclic, aliphatic, araliphatic or aromatic radical having in each case from 1 to 16 carbon atoms, where individual carbon atoms are optionally, independently of one another, replaced by a heterogroup selected from the group consisting of —O— and >N— and two or all three radicals are optionally joined to one another to form a chain comprising at least four atoms.

16. The process according to claim 15, wherein the radicals $R^1$ to $R^3$ are selected independently from the group consisting of $C_1$-$C_{12}$-alkyl, $C_5$-$C_8$-cycloalkyl, benzyl, and phenyl.

17. The process according to claim 16, wherein the radicals $R^1$ to $R^3$ are selected independently from the group consisting of $C_5$-$C_8$-alkyl.

18. A process for obtaining formic acid by thermal separation comprising:
(a) combining methyl formate, water and tertiary amine (I), which is reacted at a temperature of from 50 to 200° C., to provide a liquid stream comprising formic acid, methanol, water and tertiary amine (I) of step (a);
(b) removing from 10 to 100% by weight of the methanol formed in step (a) from the liquid stream of step (a); and
(c) removing formic acid from a liquid stream obtained from step (b) in a distillation apparatus at a temperature at the bottom of from 100 to 300° C. and a pressure of from 30 to 3000 hPa abs, wherein, in step (a), the combining of methyl formate, water and tertiary amine (I) is conducted so the tertiary amine (I) is introduced to the methyl formate in from 2 to 100 substeps, which includes (a1) methyl formate, water and optionally tertiary amine (I) are introduced in step (a1), where a molar ratio of the tertiary amine (I) optionally introduced into step (a1), n(amine to a1), to the methyl formate introduced into step (a1), n(mefo to a1), is $$0 \leq n(\text{amine to a1})/n(\text{mefo to a1}) \leq 0.05,$$

and from 70 to 100% of the hydrolysis equilibrium possible under the prevailing conditions is set at a temperature of from 50 to 200° C., and (a2) in step (a2), tertiary amine (I) is introduced into the stream obtained in step (a1), where a molar ratio of the tertiary amine (I) introduced in step (a2), n(amine to a2), to n(mefo to a1) is $$0 \leq n(\text{amine to a2})/n(\text{mefo to a1}) \leq 1,$$

where the molar ratio of the total tertiary amine (I) introduced in step (a), n(amine to a), to the total methyl formate introduced into step (a), n(mefo to a), is at least 0.1.

19. The process according to claim 18, wherein, in step (a2), from 20 to 80% of the total amount of the stream n(amine to a2) is introduced in a first substep and from 20 to 80% of the total amount of the stream n(amine to a2) is introduced in a second substep, and from 70 to 100% of the hydrolysis equilibrium possible under the prevailing conditions is set before the subsequent substep.

* * * * *